US012678262B2

(12) United States Patent
    Nomura et al.

(10) Patent No.: US 12,678,262 B2
(45) Date of Patent: Jul. 14, 2026

(54) EXAMINATION MARKER AND EXAMINATION MARKER SET

(71) Applicant: TOPPAN INC., Tokyo (JP)

(72) Inventors: Saeko Nomura, Tokyo (JP); Ryo Shoda, Tokyo (JP); Junya Tanabe, Tokyo (JP)

(73) Assignee: TOPPAN INC., Tokyo (JP)

( * ) Notice: Subject to any disclaimer, the term of this patent is extended or adjusted under 35 U.S.C. 154(b) by 0 days.

(21) Appl. No.: 18/384,839

(22) Filed: Oct. 28, 2023

(65) Prior Publication Data

US 2024/0050190 A1    Feb. 15, 2024

Related U.S. Application Data

(63) Continuation of application No. PCT/JP2022/019435, filed on Apr. 28, 2022.

(30) Foreign Application Priority Data

Apr. 30, 2021    (JP) ................................. 2021-077768
Jun. 30, 2021    (JP) ................................. 2021-108931

(51) Int. Cl.
    *A61B 90/00*        (2016.01)
(52) U.S. Cl.
    CPC ...... *A61B 90/39* (2016.02); *A61B 2090/3908* (2016.02); *A61B 2090/397* (2016.02); *A61B 2090/3991* (2016.02)
(58) Field of Classification Search
    None
    See application file for complete search history.

(56) References Cited

U.S. PATENT DOCUMENTS

| | | | |
|---|---|---|---|
| 4,193,404 A | 3/1980 | Repke et al. | |
| 5,662,110 A | 9/1997 | Carr | |
| 5,983,124 A | 11/1999 | Carr | |
| 6,063,029 A | 5/2000 | Saita et al. | |
| 6,086,247 A | 7/2000 | Von Hollen | |
| 6,356,621 B1 | 3/2002 | Furumori et al. | |

(Continued)

FOREIGN PATENT DOCUMENTS

| | | |
|---|---|---|
| CN | 102159915 A | 8/2011 |
| CN | 107693839 A | 2/2018 |

(Continued)

OTHER PUBLICATIONS

International Searching Authority, "International Search Report," issued in connection with International Patent Application No. PCT/JP2022/019435, dated Jul. 12, 2022.

(Continued)

*Primary Examiner* — Christopher Koharski
*Assistant Examiner* — Farouk A Bruce
(74) *Attorney, Agent, or Firm* — Foley & Lardner LLP

(57)        ABSTRACT

An examination marker for use in diagnostic imaging using microwaves. The examination marker includes a marker main body to be attached to an examination target. The marker main body is capable of displaying, on the marker main body, an index for use in scanning the examination target marker and is deformable following the shape of the examination target. The marker main body has a relative permittivity of 10 or less to microwaves at a frequency of 1 GHz.

16 Claims, 8 Drawing Sheets

(56) References Cited

U.S. PATENT DOCUMENTS

| | | | |
|---|---|---|---|
| 7,127,826 B2 | 10/2006 | Russell | |
| 7,781,041 B2 | 8/2010 | Broyles | |
| 9,276,324 B2 | 3/2016 | Kelsey et al. | |
| 2005/0239369 A1 | 10/2005 | Clark | |
| 2009/0177077 A1* | 7/2009 | Piferi | G01R 33/3415 600/414 |
| 2009/0214852 A1 | 8/2009 | Kelsey et al. | |
| 2009/0263644 A1 | 10/2009 | Kelsey et al. | |
| 2011/0100547 A1 | 5/2011 | Kelsey et al. | |
| 2011/0223418 A1 | 9/2011 | Habassi | |
| 2012/0041432 A1 | 2/2012 | Spertell | |
| 2013/0180657 A1 | 7/2013 | Kelsey et al. | |
| 2013/0228186 A1 | 9/2013 | Ward | |
| 2014/0094678 A1 | 4/2014 | Traboulsi et al. | |
| 2014/0248784 A1* | 9/2014 | Hayashi | H05B 6/80 438/795 |
| 2015/0045663 A1* | 2/2015 | Palikaras | A61B 5/4312 600/407 |
| 2015/0335288 A1 | 11/2015 | Toth et al. | |
| 2016/0022399 A1 | 1/2016 | St. Anne et al. | |
| 2016/0317057 A1 | 11/2016 | Li et al. | |
| 2017/0100926 A1* | 4/2017 | Kano | B32B 27/308 |
| 2018/0043144 A1 | 2/2018 | Sakuma et al. | |
| 2018/0078754 A1 | 3/2018 | Perez et al. | |
| 2018/0098820 A1 | 4/2018 | Park | |
| 2018/0116757 A1 | 5/2018 | Seto | |
| 2018/0214236 A1 | 8/2018 | Leiva | |
| 2018/0308259 A1 | 10/2018 | Kimura et al. | |
| 2019/0045745 A1 | 2/2019 | Inui et al. | |
| 2020/0101278 A1 | 4/2020 | Freeman et al. | |
| 2021/0186652 A1 | 6/2021 | Tanabe et al. | |
| 2021/0330417 A1 | 10/2021 | Tode et al. | |
| 2022/0319067 A1 | 10/2022 | Kimura et al. | |

FOREIGN PATENT DOCUMENTS

| | | | |
|---|---|---|---|
| DE | 10 2010 011 589 A1 | 9/2011 | |
| EP | 0 800 788 A1 | 10/1997 | |
| JP | H11-227390 A | 8/1999 | |
| JP | 2000-160111 A | 6/2000 | |
| JP | 2004-252262 A | 9/2004 | |
| JP | 2004-347660 A | 12/2004 | |
| JP | 2006-130865 A | 5/2006 | |
| JP | 2010-018564 A | 1/2010 | |
| JP | 2020-168348 A | 10/2020 | |
| WO | WO-2006052951 A1 * | 5/2006 | A61F 13/0269 |
| WO | WO-2012/048020 A1 | 4/2012 | |
| WO | WO-2015/163129 A1 | 10/2015 | |
| WO | WO-2017/057524 A1 | 4/2017 | |
| WO | WO-2020/059861 A1 | 3/2020 | |
| WO | WO-2020/145385 A1 | 7/2020 | |

OTHER PUBLICATIONS

International Searching Authority, "Written Opinion," issued in connection with International Patent Application No. PCT/JP2022/019435, dated Jul. 12, 2022.

European Extended Search Report issued in corresponding European Patent Application No. 22795912.9 dated Jun. 14, 2024 (5 pages).

"ASTM D3330/D3330M-04 Standard Test Method for Peel Adhesion of Pressure-Sensitive Tape" (2010). American Society for Testing and Materials. (Year: 2010).

"ASTM D6862-11 Standard Test Method for 90 Degree Peel Resistance of Adhesives" (2011). American Society for Testing and Materials. (Year: 2011).

"JIS K 7361-1: 1997 Plastic—transparent material test method for total light transmittance—Part 1: Single beam method" ( 1997) Japanese Industrial Standards. (Year: 1997).

"JIS Z 0237:2009 Test methods for adhesive tapes and sheets" (2009). Japanese Industrial Standards (Year: 2009).

"Major Industrial Polymers Polyester" (2017) Britannica.com (Year: 2017).

"Polyester" (2017) Britannica.com (Year: 2017).

"Polyethylene terephthalate Key Properties" (2008) Phoenix Technologies. Retrieved from WWW.phoenixtechnologies.net/media/371 /PET%20Properties%202008.pdf (Year: 2008).

Extended European Search Report issued in corresponding European Patent Application No. 19862669.9 dated Mar. 3, 2022.

Extended European Search Report issued in corresponding European Patent Application No. 20897575.5, dated Jan. 4, 2023.

International Searching Authority, "International Search Report," issued in connection with International Patent Application No. PCT/JP2020/045239, dated Mar. 2, 2021, 7 pages.

International Searching Authority, "Written Opinion," issued in connection with International Patent Application No. PCT/JP2020/045239, dated Mar. 2, 2021, 4 pages.

Office Action issued in corresponding Chinese Patent Application No. 201980060864.3 dated Apr. 30, 2024 (24 pages).

Office Action issued in corresponding Chinese Patent Application No. 201980060864.3 dated Aug. 22, 2024 (17 pages).

Office Action issued in corresponding Chinese Patent Application No. 201980060864.3 dated Oct. 28, 2023 (22 pages).

Office Action issued in corresponding Chinese Patent Application No. 202080081126.X dated Oct. 27, 2024.

Office Action issued in corresponding Japanese Patent Application No. 2019-084622, dated Aug. 23, 2022.

Partial Supplementary European Search Report dated Oct. 14, 2021 for corresponding European Patent Application No. 19862669.9, (14 pages).

Plastic flexible packaging materials, "Polyurethane (PU)", Jul. 31, 2018, pp. 35-40.

Office Action issued in corresponding Japanese Patent Application No. 2023-517631 dated Apr. 28, 2026.

Polymer Dictionary 3rd Edition 1st printing, Jun. 30, 2025, pp. 724-727.

* cited by examiner

EXAMINATION MARKER AND EXAMINATION MARKER SET

CROSS-REFERENCE TO RELATED PATENT APPLICATIONS

This application is a continuation application filed under 35 U.S.C. § 111(a) claiming the benefit under 35 U.S.C. §§ 120 and 365(c) of International Patent Application No. PCT/JP2022/019435, filed on Apr. 28, 2022, which is based upon and claims the benefit of priority to Japanese Patent Application No. 2021-077768, filed on Apr. 30, 2021; and Japanese Patent Application No. 2021-108931, filed on Jun. 30, 2021; the disclosures of which are incorporated herein by reference in their entirety.

TECHNICAL FIELD

The present disclosure relates to an examination marker and an examination marker set for use in image diagnosis using microwaves.

BACKGROUND

As a method of examination for breast cancer, mammography using microwaves was proposed (refer to PTL 1, for example). Mammography using microwaves does not require pressure to be applied to the breast to be examined so the subject does not feel pain during examination. In addition, mammography using microwaves does not use X rays so the subject is not exposed to radiation.

CITATION LIST

Patent Literature

[PTL 1] WO 2017/057524 A.

SUMMARY OF THE INVENTION

Technical Problem

In mammography using microwaves, a subject's breast is scanned with a probe to generate a three-dimensional image of the breast. Then, based on the generated three-dimensional image, the subject is diagnosed for the presence or absence of breast cancer. In order to generate a more precise three-dimensional image of a subject's breast, it is necessary to scan the breast with a probe over a predetermined distance at each scan without omissions or overlaps. However, since scanning with a probe is manually performed by an examiner, there may occur variations in the scanning distance and omissions or overlaps of the scanning. As a result, the precision of the three-dimensional image decreases, and the accuracy of the image diagnosis also decreases. This issue is not limited to mammography using microwaves but is in common with image diagnosis of other targets to be examined with microwaves.

Solution to Problem

An examination marker for solving the foregoing issue is an examination marker for use in image diagnosis using microwaves. The examination marker includes a marker main body to be attached to the examination target. The marker main body is capable of displaying, on the marker main body, an index for use in scanning the examination target and is deformable following the shape of the examination target. The marker main body has a relative permittivity of 10 or less to microwaves at a frequency of 1 GHz.

According to the examination marker, it is possible to allow an examiner such as a doctor or an examination technician to perform scanning based on the index displayed on the marker main body. This makes it possible to increase the accuracy of scanning the breast. In addition, since the marker main body has a relative permittivity of 10 or less to microwaves at a frequency of 1 GHz, it is possible to suppress the attenuation of microwaves emitted from the probe. Accordingly, it is possible to increase the precision of the image obtained by scanning, and it is possible to increase the accuracy of image diagnosis.

In the examination marker, the marker main body includes a base film. The base film may have a tensile elongation at break of 130% or more and a 100% elongation tensile strength of 4 N/cm or less. With a tensile elongation at break and a 100% elongation strength suited for attachment to the examination target, the examination marker is easy to attach to the examination target.

In the examination marker, the marker main body may have a moisture permeability, according to JIS Z 0208-1976, of 750 g/m2 day or more at a temperature of 40° C. and a relative humidity of 90%. When the marker main body is attached to the examination target, the examination marker can suppress perspiration of the examination target.

In the examination marker, the base film may include the index, and the index may include a coordinate grid. According to this examination marker, the base film has the coordinate grid, which eliminates the need for a process or an instrument to display the index on the base film. The examiner can perform scanning with a probe along the coordinate grid. Therefore, it is possible to keep constant the distance over which the examiner performs scanning with a probe.

In the examination marker, the coordinate grid may include a plurality of grid lines that extends along a first direction in which the examination target is to be scanned and a plurality of grid lines that are aligned along a second direction orthogonal to the first direction. The plurality of grid lines may include first grid lines having a first color and second grid lines having a second color different from the first color. The first grid line and the second grid line may be alternately aligned along the second direction.

When scanning with a probe along the first direction, the examiner can alternately perform a scan along the first grid lines and a scan along the second grid lines. Accordingly, it is possible to suppress scanning by the examiner along the same grid line a plurality of times or omitting to scan a certain grid line. That is, according to the grid lines, it is possible to reduce scanning errors that might be made by the examiner.

In the examination marker, the coordinate grid includes a plurality of grid lines that extend along a first direction in which the examination target is to be scanned and are aligned along a second direction orthogonal to the first direction. The plurality of grid lines may have the same color. According to this examination marker, the plurality of grid lines can be made of the same material, and it is easy to manufacture the examination marker including the coordinate grid.

The examination marker may further include a marker indicating predetermined coordinates in the coordinate grid. According to the examination marker, it is possible to superimpose the predetermined coordinates on the examination target at a certain position.

In the examination marker, the marker main body may include: a non-conductive base film that has a front surface and includes a scanned part that is to be scanned with a probe to obtain a signal for use in image diagnosis and a peripheral part that surrounds the scanned part, as seen from a viewpoint facing the front surface; and a verification part that is positioned at the peripheral part and contains a conductive resin composition. The microwave transmittance of the verification part may be lower than the microwave transmittance of the base film.

According to the examination marker, it is possible to determine the authenticity of the examination marker by scanning the peripheral part of the base film with a probe emitting microwaves and checking if there is a portion of the peripheral part where the received signal is attenuated.

In the examination marker, the verification part may be a print layer, and the print layer may be made of a cured body of the transparent conductive resin composition. According to this examination marker, the verification part included in a genuine examination marker is unlikely to be noticed, thus discriminating a genuine examination marker and a false examination marker by the presence or absence of the verification part increases the possibility that the discrimination result is correct.

In the examination marker, the verification part may include a first print layer and a second print layer that covers the first print layer, as seen from a viewpoint facing the front surface. The first print layer may be a cured body of the colored conductive resin composition, and the second print layer may be a cured body of a non-conductive resin composition that has a color capable of concealing the first print layer.

According to the examination marker, since the resin composition forming the first print layer is unlikely to be limited by the color of the resin composition, it is possible to increase the degree of freedom to select the resin composition for forming the first print layer. In addition, since the first print layer is concealed by the second print layer, the conductive verification part included in a genuine examination marker is unlikely to be noticed. Accordingly, discriminating a genuine examination marker and a false examination marker by the presence or absence of the verification part increases the probability that the discrimination result is correct.

In the examination marker, the verification part may include a first print layer and a pair of second print layers. In the thickness direction of the first print layer, the pair of second print layers may sandwich the first print layer. The first print layer may be a cured body of the colored conductive resin composition. The second print layers may be cured bodies of a non-conductive resin composition. The second print layers may be capable of concealing the first print layer.

According to the examination marker, since the first print layer is sandwiched between the pair of second print layers, the presence of the first print layer between the pair of second print layers is concealed by the second print layers even when the examination marker is observed from either the front or back side of the examination marker. Therefore, the conductive first print layer included in the examination marker is unlikely to be detected.

In the examination marker, as seen from a viewpoint facing the front surface, the base film may have a square shape, the peripheral part may have an annular shape including the edge of the base film, and the verification part may be positioned at a corner of the base film.

According to the examination marker, it is possible to suppress the verification part from being scanned while the scanned part is scanned using a probe to obtain a signal for generating an image. Accordingly, it is possible to suppress noise in the generated image resulting from the scanning of the verification part.

An examination marker set for solving the foregoing issue includes: the above-described examination marker; and an auxiliary marker that is positioned between the examination marker and an examination target at the time of image diagnosis using microwaves and is pressed by the examination marker toward the examination target. The verification part is a first verification part. The auxiliary marker includes a non-conductive marker main body, a protective film that is laminated on the marker main body so as to be peelable from the marker main body, and a second verification part that is positioned on the protective film. The microwave transmittance of the second verification part is lower than the microwave transmittance of a laminated body of the marker main body and the protective film.

According to the examination marker set, like the examination marker, it is possible to determine the authenticity of the auxiliary marker and the authenticity of a combination of the examination marker and the auxiliary marker by scanning the auxiliary marker with a probe.

Advantageous Effects of the Invention

According to the present disclosure, it is possible to increase the accuracy of image diagnosis.

DETAILED DESCRIPTION

First Embodiment

A first embodiment of an examination marker will be described with reference to FIGS. 1 to 7. In the present embodiment, the examination marker is a marker for use in mammography that is an example of image diagnosis using microwaves. The examination marker is a marker that is attached to a breast to be examined by mammography.

[Examination Marker]

The examination marker will be described with reference to FIGS. 1 to 4. The examination marker includes a marker main body. The marker main body is capable of displaying an index for use in scanning a breast and can deform to follow the shape of the breast. The marker main body is attached to the breast. The marker main body has a relative permittivity of 10 or less to microwaves at a frequency of 1 GHz. Hereinafter, a first example of the examination marker will be described with reference to FIG. 1, and a second example of the examination marker will be described with reference to FIG. 2. Then, configuration common to the first example of the examination marker and the second example of the examination marker will be described with reference to FIGS. 3 and 4.

First Example

Figure 1:
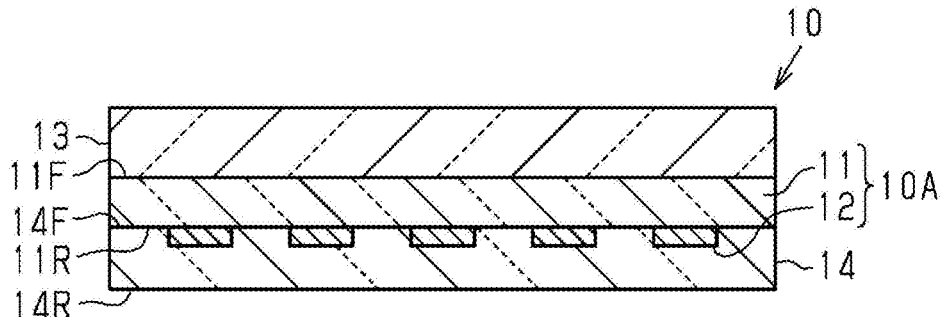
FIG. 1 is a cross-sectional view of a structure of a first example of an examination marker in a first embodiment.

As shown in FIG. 1, the first example of an examination marker 10 includes a base film 11 as an example of a marker main body 10A. The base film 11 has a coordinate grid 12 for guiding the user to the scanning position on an examination target. The coordinate grid 12 is an example of an index for scanning. The marker main body 10A satisfies the following condition 1-1.

(Condition 1-1) The relative permittivity to microwaves at a frequency of 1 GHz is 10 or less. The relative permittivity to microwaves is measured by the zero method. The zero method is a method in conformity with JIS C 2138: 2007 "Electrical insulating materials—Methods for the determination of the relative permittivity and dielectric dissipation factor".

According to the examination marker 10, it is possible to allow an examiner such as a doctor or a clinical technician to perform scanning based on the index displayed on the marker main body 10A. This increases the accuracy of scanning the breast. In addition, since the marker main body 10A has a relative permittivity of 10 or less to microwaves at a frequency of 1 GHz, it is possible to suppress attenuation of the microwaves emitted from the probe. Accordingly, it is possible to increase the precision of an image obtained as a scanning result, and as a result, it is possible to increase the accuracy of image diagnosis.

The base film 11 has the coordinate grid 12, which eliminates the need for a process or an instrument to display the index on the base film 11. The examiner can perform scanning with a probe along the coordinate grid 12. Therefore, it is possible to keep constant the distance over which the examiner performs scanning with a probe.

The base film 11 preferably satisfies the following condition:

(Condition 1-2) The base film 11 has a tensile elongation at break of 130% or more and a 100% elongation tensile strength of 4 N/cm or less.

The marker main body 10A preferably satisfies the following condition:

(Condition 1-3) The moisture permeability according to JIS Z 0208-1976 is 750 g/m2 day or more at a temperature of 40° C. and a relative humidity of 90%.

The base film 11 has a tensile elongation at break and an 100% elongation tensile strength suited for attachment to the examination target. Thus, according to the base film 11, it is easy to attach the examination marker 10 to the examination target.

The tensile elongation at break can be determined in conformity with JIS K 7161-1: 2014 (ISO 527-1) "Plastics—Determination of tensile properties—Part 1: General principles", and JIS K 7127: 1999 (ISO 527-3) "Plastics—Determination of tensile properties—Part 3: Test conditions for films and sheets". If the measurement target has no yield point, the tensile breaking strain is measured. If the measurement target has a yield point, the nominal strain at tensile fracture is measured. These measurement values can be used to determine the tensile elongation at break.

The 100% elongation tensile strength is obtained by measuring the magnitude of a force applied to a test piece when the strain on the test piece has reached a prescribed value (100%) and dividing the magnitude of the force by the width of the test piece, as defined in JIS K 7161-1: 2014 (ISO 527-1) "Plastics—Determination of tensile properties—Part 1: General principles". The 100% elongation tensile strength (T) (N/cm) can be determined by the following equation:

$$T = F / W$$

where F is the measured magnitude (N) of the force, and W is the width (cm) of the test piece.

The moisture permeability is measured by a method in conformity with JIS Z 0208-1976 "Testing Methods for Determination of the Water Vapour Transmission Rate of Moisture—Proof Packaging Materials". Since the moisture permeability of the marker main body 10A satisfies the condition 1-3, when the marker main body 10A is attached to the examination target, it is possible to suppress perspiration of the examination target.

The marker main body 10A can include a part of which the total light transmittance defined in JIS K 7361-1: 1997 HPlastics—Determination of the total luminous transmittance of transparent materials—Part 1: Single beam instrument" is 30% or more. This makes it possible to grasp the state of the surface of the breast via the part of the marker main body 10A with a total light transmittance of 30% or more. In the present embodiment, the part of the marker main body 10A other than the coordinate grid 12 is a transmission part with a total light transmittance of 30% or more. Therefore, it is possible to specify the positions of moles and spots on the breast by visual examination or camera via the transmission part. Since moles and spots on the breast do not change in position, the positions of moles and spots on the breast are important in locating a lesion in the breast.

The base film 11 is made of a synthetic resin. The synthetic resin for forming the base film 11 may be a polyurethane resin, for example. This makes it possible to obtain the base film 11 that has excellent bonding adaptability and high moisture permeability. The thickness of the base film 11 may be 5 μm or more and 30 μm or less, for example. A base film 11 that is thin and made of a polyurethane resin can be stretched well even with a small external force applied to the base film 11 for stretching the base film 11. Thus, the base film 11 can exhibit a high capability of following the shape of the breast and high adhesion to the breast.

The base film 11 may be made of a synthetic resin other than a polyurethane resin as far as the base film 11 has a relative permittivity of 10 or less to microwaves at a frequency of 1 GHz. Examples of a synthetic resin other than a polyurethane resin include polyvinylidene fluoride resin, ethylene-vinyl acetate copolymer resin, polypropylene resin, polyethylene terephthalate resin, and the like.

The base film 11 includes a front surface 11F and a rear surface 11R opposite to the front surface 11F. The front surface 11F is the surface to be scanned with a probe during examination of the examination target. In the present embodiment, the coordinate grid 12 is positioned on the rear surface 11R.

The examination marker 10 further includes a release film 13 and a protective film 14. The release film 13 is laminated in a peelable manner on the front surface 11F of the base film 11. The protective film 14 is laminated in a peelable manner on the rear surface 11R of the base film 11.

The protective film 14 covers the rear surface 11R of the base film. Accordingly, the coordinate grid 12 is sandwiched between the base film 11 and the protective film 14, and the coordinate grid 12 is not exposed to the outer surface of the examination marker 10. Thus, the coordinate grid 12 is unlikely to become detached from the base film 11. The protective film 14 covers the entire base film 11 as seen from a viewpoint facing the base film 11. The surface of the protective film 14 in contact with the base film 11 is a front surface 14F, and the surface of the protective film 14 opposite to the front surface 14F is a rear surface 14R. In other words, the surface of the protective film 14 opposite to the front surface 14F is the rear surface 14R. The protective film 14 has a thickness to a degree that the entire coordinate grid 12 is covered and the rear surface 14R is a substantially flat surface.

In the examination marker 10, the rear surface 11R of the base film 11 is attached to the examination target. In the examination marker 10, the release film 13 and the protective film 14 sandwich the base film 11 in the thickness direction of the base film 11. Thus, the base film 11 is protected from the outside by the release film 13 and the protective film 14 until immediately before the base film 11 is attached to the examination target. Therefore, the base film 11 is kept clean until it is attached to the examination target.

Each of the release film 13 and the protective film 14 is preferably a transparent or translucent film made of a synthetic resin. Each of the release film 13 and the protective film 14 is formed of a base film and a release layer, for example. The release layer is laminated on the base film. The release layer of the release film 13 is in contact with the front surface 11F of the base film 11. The release layer of the protective film 14 is in contact with the rear surface 11R of the base film 11. The base film may be a polyethylene terephthalate film or the like, for example. The release layer may be a layer made of a silicone resin, for example. Each of the release film 13 and the protective film 14 may be formed of only a base film, and the surface of the base film in contact with another layer may be processed for enhancing peeling capability.

A part of the release film 13 may be subjected to half-cut processing. In other words, the release film 13 may have a slit that extends from the front surface of the release film 13 to the middle of the release film 13 in the thickness direction of the release film 13. The surface of the release film 13 opposite to the surface in contact with the base film 11 is the front surface.

Second Example

Figure 2:
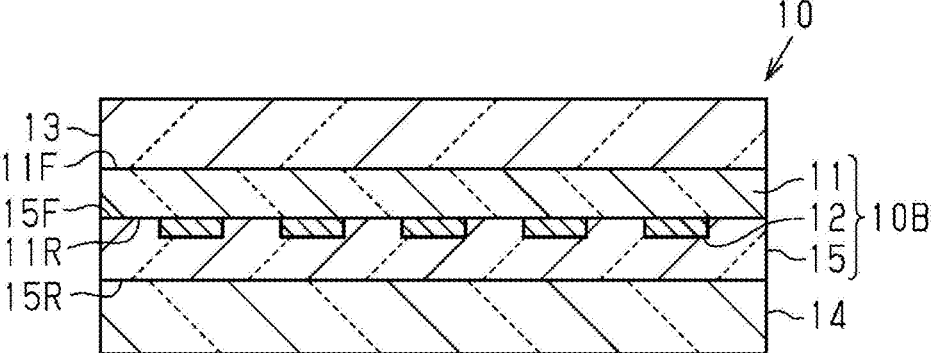
FIG. 2 is a cross-sectional view of a structure of a second example of the examination marker in the first embodiment.

As shown in FIG. 2, a second example of the examination marker 10 further includes an adhesive layer 15 in addition to the base film 11, the release film 13, and the protective film 14. In the second example of the examination marker 10, a marker main body 10B includes a base film 11 and an adhesive layer 15. The adhesive layer 15 is laminated on the base film 11. The adhesive layer 15 is attached to the breast. The second example of the examination marker 10 satisfies the condition 1-1 as the first example of the examination marker 10 does. The second example of the examination marker 10 preferably satisfies at least one of the condition 1-2 and the condition 1-3. That is, the second example of the examination marker 10 may satisfy only the condition 1-2, may satisfy only the condition 1-3, or may satisfy both the condition 1-2 and the condition 1-3. In the marker main body 10B, different layers have the function to display an index and the function to attach to the examination target. Thus, it is possible to increase the degree of freedom to select the material for forming the examination marker as compared to the case where one layer has the function to display an index and the function to attach to the examination target.

The adhesive layer 15 covers the rear surface 11R of the base film 11. Accordingly, even when the coordinate grid 12 is sandwiched between the base film 11 and the adhesive layer 15, the coordinate grid 12 does not constitute the outer surface of the examination marker 10. Thus, the coordinate grid 12 is unlikely to become detached from the base film 11. The adhesive layer 15 covers the entire base film 11 as seen from a viewpoint facing the adhesive layer 15. The surface of the adhesive layer 15 in contact with the base film 11 is a front surface 15F, and the surface of the adhesive layer 15 opposite to the front surface 15F is a rear surface 15R. That is, the surface of the adhesive layer 15 opposite to the front surface 15F is the rear surface 15R. The front surface 15F of the adhesive layer 15 is in contact with the base film 11, and the rear surface 15R of the adhesive layer 15 is in contact with the protective film 14.

The adhesive layer 15 has a thickness to a degree that the entire coordinate grid 12 is covered and the rear surface 15R is substantially flat. In the examination marker 10, the rear surface 15R of the adhesive layer 15 is attached to the subject. The thickness of the adhesive layer 15 may be 5 μm or more and 25 μm or less, for example.

The release film 13 and the protective film 14 sandwich the marker main body 10B in the thickness direction of the base film 11. Thus, the marker main body 10B is protected from the outside by the release film 13 and the protective film 14 until immediately before the marker main body 10B is attached to the subject. Accordingly, the marker main body 10B is kept clean until the marker main body 10B is attached to the subject.

The adhesive layer 15 is made of a synthetic resin as the base film 11 is. The synthetic resin for forming the adhesive layer 15 may be a polyurethane resin, for example. Forming the adhesive layer 15 from a polyurethane resin makes it possible to provide the adhesive layer 15 with high moisture permeability. The adhesive layer 15 may be made of a synthetic resin other than a polyurethane resin as far as the relative permittivity to microwaves at a frequency of 1 GHz of the marker main body 10B is 10 or less.

[Coordinate Grid]

Hereinafter, the coordinate grid 12 will be described in more detail with reference to FIGS. 3 and 4. A first example of the coordinate grid will be described with reference to FIG. 3, and a second example of the coordinate grid will be described with reference to FIG. 4.

First Example

Figure 3:
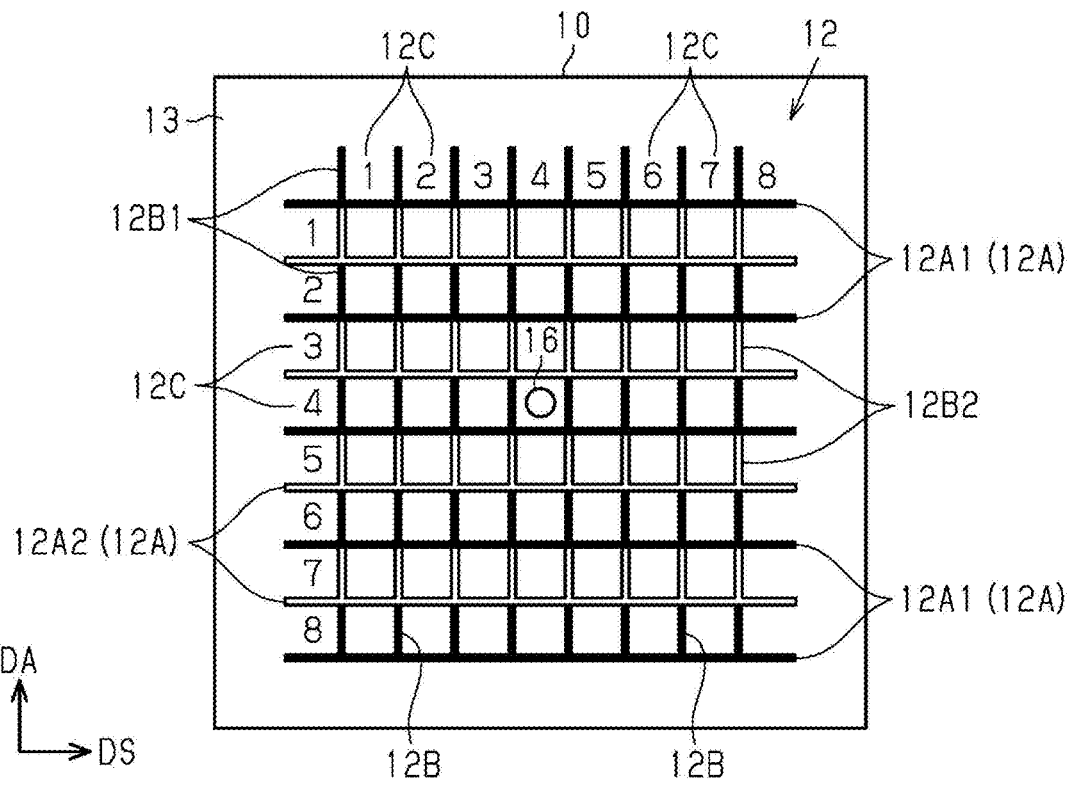
FIG. 3 is a plan view of a structure of an examination marker including a first example of a coordinate grid in a plan view facing the front surface of the examination marker.

As shown in FIG. 3, the coordinate grid 12 includes a plurality of grid lines 12A. Each of the grid lines 12A extends along a scanning direction DS, and the plurality of grid lines 12A are aligned in an arrangement direction DA orthogonal to the scanning direction DS. In the present embodiment, the horizontal direction in the plane of paper is the scanning direction DS. The scanning direction DS is an example of a first direction, and the arrangement direction DA is an example of a second direction. The scanning direction DA is the direction in which the examiner scans an examination target using a probe. In the present embodiment, the arrangement direction DA is the vertical direction in the plane of paper. In the arrangement direction DA, first grid lines 12A1 having a first color and second grid lines 12A2 having a second color are alternately aligned. The second color is different from the first color.

In performing scanning with a probe along the scanning direction DS, the examiner can alternately perform scanning along the first grid lines 12A1 and scanning along the second grid lines 12A2. Accordingly, it is possible to prevent the examiner from scanning along the same grid line 12A a plurality of times or omitting to perform scanning along a certain grid line 12A. That is, according to the grid lines 12A, it is possible to reduce scanning errors that might be made by the examiner.

The first grid lines 12A1 may be red, for example, and the second grid lines 12A2 may be blue, for example. The first color that is the color of the first grid lines 12A1 and the second color that is the color of the second grid lines 12A2 are not limited to red and blue and can be arbitrarily set as long as they are different colors.

The coordinate grid 12 further includes a plurality of grid lines 12B that extends along the arrangement direction DA and are aligned along the scanning direction DS. The plurality of grid lines 12B forms a square grid together with the plurality of grid lines 12A described above, as seen from a viewpoint facing a plane over which the examination marker 10 extends. In each grid line 12B, first segments 12B1 and second segments 12B2 are alternately aligned. In the arrangement direction DA, the first segments 12B1 and the second segments 12B2 are segmented in each section sandwiched between one first grid line 12A1 and one second grid line 12A2 adjacent to each other. The first segments 12B1 have the first color, as the first grid lines 12A1 do. The second segment 12B2 have the second color, as the second grid lines 12A2 do.

The coordinate grid 12 further includes positional markers 12C. In the present embodiment, the positional markers 12C are numbers for use in specifying the position on the coordinate grid 12. The positional markers 12C include a plurality of numbers aligned along the scanning direction DS, for example. The plurality of numbers is positioned outside of the first grid line 12A1 that is positioned at the upper end in the arrangement direction DA. Each of the numbers is positioned between two grid lines 12B or is positioned outside of the grid line 12B that is positioned at the end in the scanning direction DS. The positional markers 12C include a plurality of numbers aligned along the arrangement direction DA, for example. The plurality of numbers is positioned outside of the grid line 12B that is positioned at the left end in the scanning direction DS. Each of the numbers is positioned between two grid lines 12A in the arrangement direction DA. The positional markers 12C are not limited to a plurality of numbers and may include a plurality of characters, for example.

Since the coordinate grid 12 includes the positional markers 12C, the accuracy of the examination can be further improved by the examiner referring to the positional markers 12C. If a lesion is found in the breast, the positional markers 12C can be used to specify the position of the lesion in the breast.

The coordinate grid 12 is printed using ink on the rear surface 11R of the base film 11. The ink for printing the coordinate grid 12 can be any ink that is capable of being printed on the base film 11.

The examination marker 10 further includes a marker 16 that indicates a predetermined position on the coordinate grid 12. In the present embodiment, the predetermined position is the center of the coordinate grid 12. The marker 16 is a circular point that is positioned in the center of the coordinate grid 12. The shape of the marker 16 is not limited to a circle and can be arbitrarily set. The marker 16 may be formed by a plurality of portions separated from each other. As far as the marker 16 indicates the center of the coordinate grid 12, the marker 16 may be arranged at a position shifted from the center of the coordinate grid 12. The marker 16 may be printed using ink on the rear surface 11R of the base film 11 as the coordinate grid 12 is.

According to the marker 16, at the time of use of the examination marker 10, coordinates indicated by the marker 16 can be superimposed on the breast at the specific position. According to the present embodiment, when the examiner attaches the examination marker 10 to the breast such that the marker 16 is positioned at the nipple of the breast, the coordinate grid 12 can be positioned in the entire surrounding area of the nipple. Accordingly, the examiner can scan the entire breast in the circumferential direction of the nipple.

Second Example

Figure 4:
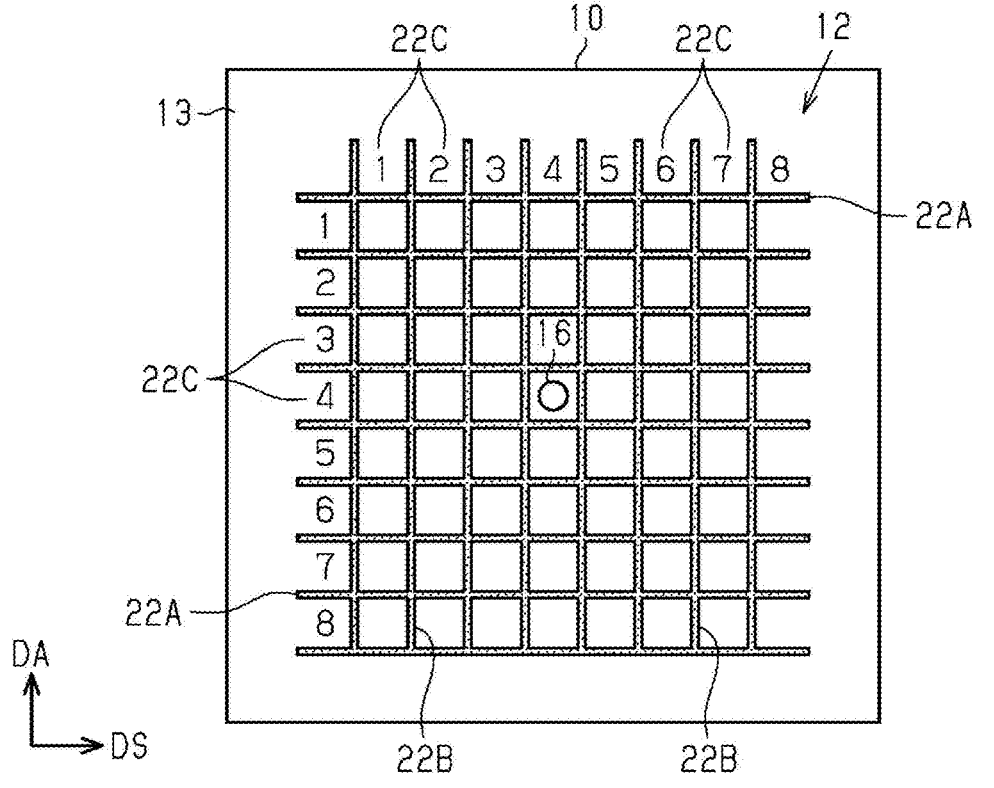
FIG. 4 is a plan view of a structure of an examination marker including a second example of the coordinate grid in a plan view facing the front surface of the examination marker.

As shown in FIG. 4, the coordinate grid 12 includes a plurality of grid lines 22A. Each of the grid lines 22A extends along the scanning direction DS, and the plurality of grid lines 22A is aligned along the arrangement direction DA orthogonal to the scanning direction DS. The plurality of grid lines 22A has the same color. Thus, the plurality of grid lines 22A can be formed of the same material, which makes it easy to manufacture the examination marker 10.

The coordinate grid 12 further includes a plurality of grid lines 22B that extends along the arrangement direction DA and is aligned along the scanning direction DS. The plurality of grid lines 22B forms a square grid together with the grid lines 22A described above, as seen from a viewpoint facing a plane over which the examination marker 10 extends. The plurality of grid lines 22B have the same color as that of the grid lines 22A described above.

As the coordinate grid 12 in the first example does, the coordinate grid 12 includes positional markers 22C and a marker 16. In the coordinate grid 12, the positional markers 22C and the marker 16 have the same color as that of the grid lines 22A.

As described above, in the coordinate grid 12, since not only the grid lines 22A and 22B have the same color but also the positional markers 22C and the marker 16 have the same color as that of the grid lines 22A, the positional markers 22C and the marker 16 can be formed of the same material as that of the grid lines 22A.

In the plurality of grid lines 22A, adjacent grid lines 22A may be made different in external appearance. Accordingly, it is possible to prevent scanning errors that might be made by the examiner, as in the case where the colors of adjacent grid lines 22A in the coordinate grid 12 are made different.

In the case of making different the outer appearances of adjacent grid lines 22A, solid grid lines 22A and broken grid lines 22A may be alternately arranged, for example. In this case, in the plurality of grid lines 22B, solid grid lines 22B and broken grid lines 22B may be alternately arranged as well.

In the coordinate grid 12, the plurality of grid lines 22A may be arranged at intervals of the same width as the width of the grid lines 22A in the arrangement direction DA. In this case, the grid lines 22A preferably have a width similar to the distance between two grid lines 22A shown in FIG. 4, for example. In this case, the grid lines 22A may be formed by solid printing or may be formed by a plurality of dots. Accordingly, since the grid lines 22A and the transparent parts are alternately positioned in the coordinate grid 12, it is possible to prevent scanning errors that might be made by the examiner as in the case with the coordinate grid 12.

In the coordinate grid 12 of the second example, the color of the coordinate grid 12 may be white, for example. In this case, as a white pigment for forming the coordinate grid 12, barium titanate may be used, for example. Barium titanate is more preferable than titanium oxide that is used as a white pigment like barium titanate, from a viewpoint of low catalyst activity. In the case of using barium titanate as a white pigment, in a predefined volume of the base film and the barium titanate, the volume of the barium titanate is preferably 20 volume % or less, where the sum of the volume of the base film and the volume of barium titanate is 100 volume %.

[Method of Using Examination Marker]

How to use the examination marker 10 will be described with reference to FIGS. 5 to 7. The method of using the first example of the examination marker 10 will be described with reference to FIG. 5, and how to use the second example of the examination marker 10 will be described with reference to FIG. 6. Whether the examination marker 10 includes the coordinate grid 12 of the first example or the examination marker 10 includes the coordinate grid 12 of the second example, the method of using the examination marker 10 described below is the same. Thus, hereinafter, method of using the examination marker 10 including the first example of the coordinate grid 12 will be described as an example.

Figure 5:
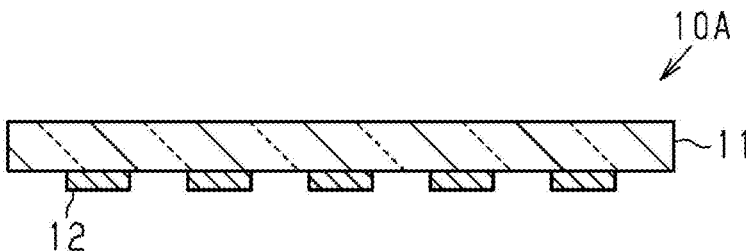
FIG. 5 is a cross-sectional view of a structure of a marker main body in using the examination marker in the first example.

As shown in FIG. 5, in the case of using the first example of the examination marker 10, first, the user peels off the release film 13 and the protective film 14 from the base film 11. In the case of using the first example of the examination marker 10, the release film 13 may be peeled off earlier than the protective film 14, or the protective film 14 may be peeled off earlier than the release film 13.

Figure 6:
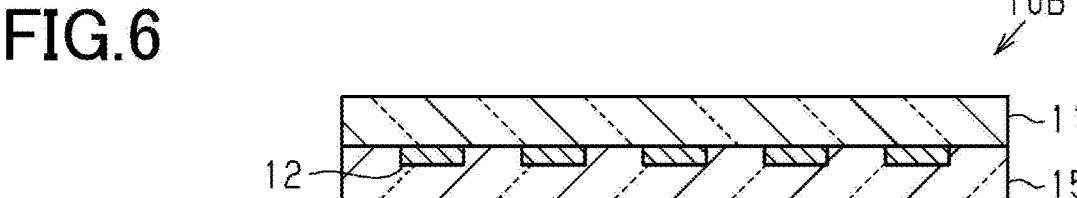
FIG. 6 is a cross-sectional view of a structure of a marker main body in using the examination marker in the second example.

As shown in FIG. 6, in the case of using the second example of the examination marker 10, the user peels off the release film 13 from the base film 11 and peels off the protective film 14 from the adhesive layer 15. As in the case of using the first example of the examination marker 10, the release film 13 may be peeled off earlier than the protective film 14, or the protective film 14 may be peeled off earlier than the release film 13.

Figure 7:
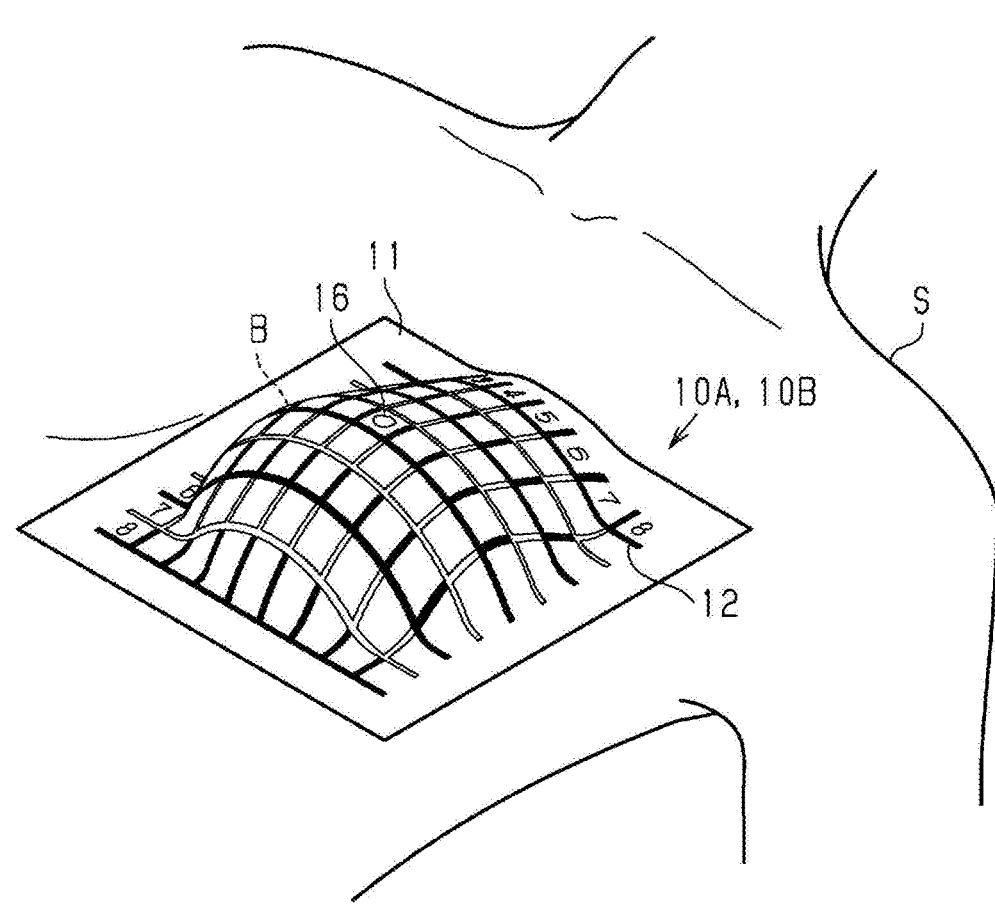
FIG. 7 is a schematic diagram for describing a method for using the examination marker.

As shown in FIG. 7, the marker main body 10A, 10B is attached to a breast B of a subject S. At this time, the examination marker 10 is attached to the breast B so as to overlap the nipple. In the present embodiment, since the marker 16 is positioned in the center of the coordinate grid 12, overlapping the marker 16 and the nipple allows a part of the coordinate grid 12 to be positioned on the entire nipple in the circumferential direction. Accordingly, the entire breast B can be easily scanned using the coordinate grid 12 as a guide.

In attaching the marker main body 10A, 10B to the breast B, the position of the marker 16 is aligned with the position of the nipple while the four sides constituting the edge of the laminated body are pulled outward. Then, gradually attaching the laminated body from the upper end to lower end of the marker main body 10A, 10B to the breast B suppresses the base film 11 from becoming wrinkled. The upper end of the marker main body 10A, 10B is positioned on the upper side of the nipple, and the lower end of the marker main body 10A, 10B is positioned on the lower side of the nipple. If the base film 11 becomes wrinkled, the portion of the marker main body 10A, 10B including the wrinkles in the base film 11 is peeled from the breast B, and the marker main body 10A, 10B is attached again to the breast B while a force pulling the base film 11 toward the outside of the edge is applied to the marker main body 10A, 10B. This removes the wrinkles from the base film 11.

In attaching the marker main body 10A, 10B to the breast B, a jig for pulling the marker main body 10A, 10B toward the outside of the edge of the marker main body 10A, 10B may be used. As described above, if the release film 13 is subjected to a half-cutting process, the marker main body 10A, 10B may be attached to the breast B in the procedure described below. That is, the protective film 14 is peeled off from the marker main body 10A, 10B, and then the laminated body of the release film 13 and the marker main body 10A, 10B is attached to the breast B. Then, the release film 13 may be peeled off from the base film 11.

As described above, in the present embodiment, the grid lines 12A extending along the scanning direction DS include the first grid lines 12A1 and the second grid lines 12A2 having different colors, and the first grid lines 12A1 and the second grid lines 12A2 are alternately aligned in the arrangement direction DA. Thus, in performing scanning with a probe along the scanning direction DS, the examiner can alternately perform the scanning along the first grid lines 12A1 and the scanning along the second grid lines 12A2. Accordingly, it is possible to suppress the examiner from scanning along the same grid line 12A a plurality of times or omitting to scan along a certain grid line 12A. That is, according to the grid lines 12A, it is possible to reduce scanning errors that might be made by the examiner.

EXAMPLES

Examples and comparative example will be described with reference to Table 1.

Example 1

A polyurethane (PU) film with a thickness of 300 μm was formed by extrusion film formation using urethane elastomer (Elastollan C60A produced by BASF SE) (Elastollan is a registered trademark).

Example 2

A film with a thickness of 300 μm was obtained by extrusion film formation using a master batch in which barium titanate (BaTiO3) as a high-dielectric filler was added to the urethane elastomer (the same as described above) such that the volume of the fraction barium titanate was 15 volume %.

Example 3

A film with a thickness of 300 μm was obtained by the same film formation method as Example 2, except that barium titanate was added to the urethane elastomer (the same as described above) such that the volume fraction of the barium titanate was 20 volume % in Example 2.

Comparative Example 1

A film with a thickness of 300 μm was obtained by the same film formation method as Example 2, except that barium titanate was added to the urethane elastomer (the same as described above) such that the volume fraction of the barium titanate was 30 volume % in Example 2.
[Evaluation Method]
[Measurement of Relative Permittivity]

An RF impedance/material analyzer (E4991A produced by Agilent Technologies, Inc.) and dielectric material measurement electrodes (16453A produced by Agilent Technologies, Inc.) were prepared. The films of Examples 1 to 3 and Comparative Example 1 were inserted into between the electrodes to measure distribution of permittivity in the frequency range of 1 MHz to 1 GHz. At this time, the relative permittivity of each film was measured by a method in conformity with JIS C 2138: 2007 "Electrical insulating materials—Methods for the determination of the relative permittivity and dielectric dissipation factor". The values of relative permittivity at a frequency of 1 GHz were read from distribution data displayed on the screen of the RF impedance/material analyzer.
[Evaluation Results]

Table 1 shows the measurement results of relative permittivity of the examination markers of Examples 1 to 3 and Comparative Example 1 as follows:

TABLE 1

|  | Material | Volume fraction (vol %) | Relative permittivity |
|---|---|---|---|
| Example 1 | PU | 0 | 4.1 |
| Example 2 | PU, BaTiO$_3$ | 15 | 6.0 |
| Example 3 | PU, BaTiO$_3$ | 20 | 7.8 |
| Comparative Example 1 | PU, BaTiO$_3$ | 30 | 13.9 |

As shown in Table 1, it was confirmed that the relative permittivity of the film in Example 1 was 4.1, the relative permittivity of the film in Example 2 was 6.0, the relative permittivity of the film in Example 3 was 7.8, and the relative permittivity of the film in Comparative Example 1 was 13.9.

As a result of scanning with microwaves via each film, it was confirmed that the films in Examples 1 to 3 make it possible to obtain an accurate microwave signal for generating a three-dimensional image that is capable of breast diagnosis. In contrast to this, it was confirmed that the film in Comparative Example 1 did not make it possible to obtain an accurate microwave signal for generating a three-dimensional image that is capable of breast diagnosis.

In addition, it was confirmed that the film preferably contains barium titanate at 20 volume % or less, from a viewpoint of satisfying the condition that the relative permittivity to microwaves at a frequency of 1 GHz is 10 or less.

As described above, according to the first embodiment of the examination marker, it is possible to obtain the following advantageous effects.

(1-1) Since it is possible to allow the examiner to perform scanning based on the index displayed on the marker main body 10A, 10B, it is possible to increase the accuracy of scanning the examination target. In addition, since the marker main body 10A, 10B has a relative permittivity of 10 or less to microwaves at a frequency of 1 GHz, it is possible to suppress the attenuation of microwaves emitted from the probe. Accordingly, it is possible to increase the precision of the image obtained by the scanning, and as a result, it is possible to increase the accuracy of the image diagnosis.

(1-2) With the tensile elongation at break and the 100% elongation strength suited for attachment to the examination target, the examination marker is easy to attach to the examination target.

(1-3) When the marker main body 10A, 10B is attached to the examination target, it is possible to suppress perspiration of the examination target.

(1-4) There is no need for a process or an instrument to display the index on the base film 11. The examiner can perform scanning with a probe along the coordinate grid 12. Therefore, it is possible to keep the distance constant over which the examiner performs scanning with a probe.

(1-5) According to the grid lines 12A, it is possible to reduce scanning errors that might be made by the examiner.

(1-6) At the time of use of the examination marker 10, it is possible to superimpose the coordinates indicated by the marker 16 on the breast B at a certain position.

The first embodiment described above can be carried out in a modified manner as described below.
[Marker Main Body]

The part of the marker main body 10A, 10B other than the coordinate grid 12 may have a total light transmittance of less than 30%. Even in this case, as far as the marker main body 10A, 10B has a relative permittivity of 10 or less to microwaves at a frequency of 1 GHz, it is possible to obtain an advantageous effect corresponding to (1-1) described above. The total light transmittance of the coordinate grid 12 may be 30% or higher. In this case, it is possible to understand the state of the surface of the breast B via the coordinate grid 12.

The marker main body 10A, 10B may not have an index as exemplified by the coordinate grid 12. In this case, the marker main body 10A, 10B can display an index by a projector projecting various images onto the marker main body 10A, 10B. Also in this case, it is possible to obtain an advantageous effect corresponding to (1-1) described above.

The marker main body 10A, 10B may have a shape other than a square shape. The marker main body 10A, 10B may have a geometrical shape such as an oval shape, a circular shape, and a triangular shape, or an unstable shape other than geometrical shapes, for example.

The marker main body may have a multi-layer structure formed of three or more layers. Even in this case, the marker main body can display an index. In addition, as far as the relative permittivity of the marker main body to microwaves at a frequency of 1 GHz is 10 or less, it is possible to obtain an advantageous effect corresponding to (1-1) described above.

[Coordinate Grid]

The coordinate grid 12 may have a shape other than a square grid. For example, the coordinate grid 12 may have a shape corresponding to polar coordinates that are formed by a plurality of concentric circles with different diameters.

The coordinate grid 12 may not have the grid lines 12B. The coordinate grid 12 having at least the grid lines 12A can suppress scanning errors that might be made by the examiner. That is, the base film 11 may have not only the coordinate grid 12 but also a scanning index of another shape such as a shape extending along one direction. The scanning index can guide the user to the position where scanning is to be performed with a probe or guide the user in the scanning direction, for example.

The coordinate grid 12 may not have the positional markers 12C. The coordinate grid 12 having at least the grid lines 12A can suppress scanning errors that might be made by the examiner.

The marker main body 10A, 10B may have not only the coordinate grid 12 but also a scanning index having a graphic pattern extending along one direction or an index of numbers or characters, for example. The scanning index can suggest the position where scanning is to be performed with a probe or suggesting the scanning direction, for example.

The coordinate grid 12 may not be formed by printing. For example, the coordinate grid 12 may be formed by concave and convex portions on the base film 11, for example.

[Sign]

The marker 16 may be omitted. Even in this case, as far as the marker main body 10A, 10B has the coordinate grid 12, the marker main body 10A, 10B can be attached to the breast B with adjustments made to the position of the coordinate grid 12 with respect to the breast B, so that the entire breast B can be scanned in the circumferential direction of the nipple.

The marker 16 may not be formed by printing, as in the case of the coordinate grid 12. For example, the marker 16 may be formed by concave and convex portions on the base film 11.

[Base Film]

The thickness of the base film 11 may be greater than 30 μm or smaller than 5 μm. Even in this case, as far as the relative permittivity of the marker main body 10A, 10B to microwaves at a frequency of 1 GHz is 10 or less, it is possible to obtain an advantageous effect corresponding to (1-1) described above.

The marker main body 10A, that is, the base film 11 may be attached to the breast using a self-adhesive material, for example. The self-adhesive material may be tape, for example. In this case, the region of the base film 11 outside of the scanning index is attached to the breast by the self-adhesive material. The self-adhesive material may be positioned on the rear surface 11R of the base film 11 or may be positioned on the front surface 11F of the base film 11. If the self-adhesive material is positioned on the front surface 11F of the base film 11, the self-adhesive material has a shape and size so as to extend from the base film 11 to the outside of the base film 11.

The marker main body may include the base film 11 and an attachment layer to be laminated on the base film 11.

In this case, the base film 11 and the attachment layer are separate components, and the attachment layer is laminated on the base film 11 at the time of use of the marker main body. The attachment layer is a layer that can be attached to the breast to position the base film 11 on the breast. The attachment layer may be an adhesive layer formed of the self-adhesive material described above, for example. Alternatively, the attachment layer may be a layer formed of an ointment of aliphatic hydrocarbon, for example. That is, the attachment layer may be formed of aliphatic hydrocarbon having a cream-like texture, for example.

The attachment layer may be formed by applying aliphatic hydrocarbon to the examination target at the time of use of the base film 11 and then the base film 11 may be arranged on the attachment layer. Accordingly, a laminated body of the base film 11 and the attachment layer is formed in a state where the marker main body is used.

Even in this case, the marker main body can display an index. In addition, as far as the relative permittivity of the marker main body to microwaves at a frequency of 1 GHz is 10 or less, it is possible to obtain an advantageous effect corresponding to (1-1) described above.

[Adhesive Layer]

An adhesive for forming the adhesive layer 15 may be an adhesive other than a urethane-based adhesive. For example, the adhesive for forming the adhesive layer 15 may be an acrylic adhesive.

[Release Film]

In the examination marker 10, the release film 13 may be omitted. Even in this case, the marker main body 10A, 10B can display an index. In addition, as far as the relative permittivity of the marker main body 10A, 10B to microwaves at a frequency of 1 GHz is 10 or less, it is possible to obtain an advantageous effect corresponding to (1-1) described above.

[Protective Film]

In the examination marker 10, the protective film 14 may be omitted. Even in this case, the marker main body 10A, 10B can display an index. In addition, as far as the relative permittivity of the marker main body 10A, 10B to microwaves at a frequency of 1 GHz is 10 or less, it is possible to obtain an advantageous effect corresponding to (1-1) described above.

[Examination Target]

The examination target is not limited to the breast and may be another part of the human body. That is, the examination marker 10 may be used not only for mammography but also for other image diagnosis.

Second Embodiment

Figure 8:
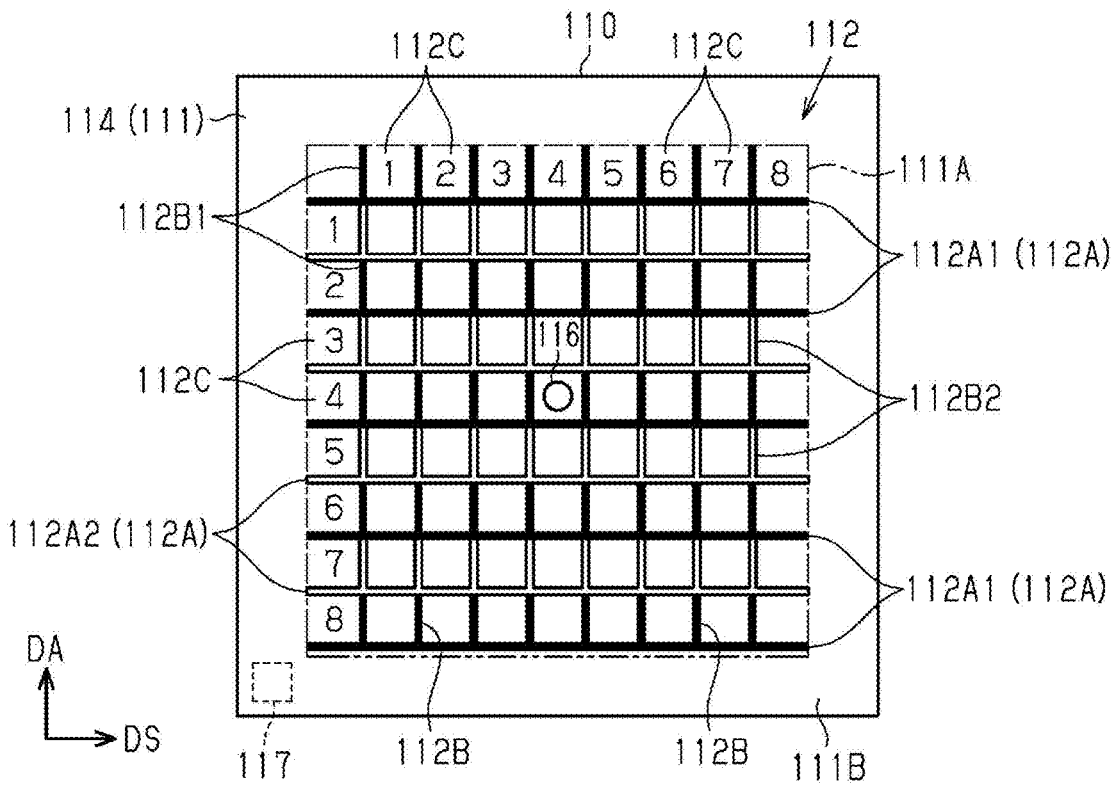
FIG. 8 is a plan view of a structure of an examination marker in a second embodiment.
Figure 9:
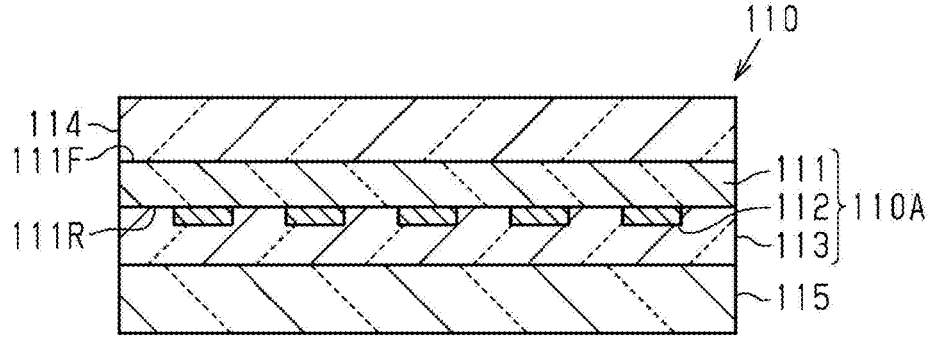
FIG. 9 is a cross-sectional view of the structure of the examination marker shown in FIG. 8.
Figure 10:
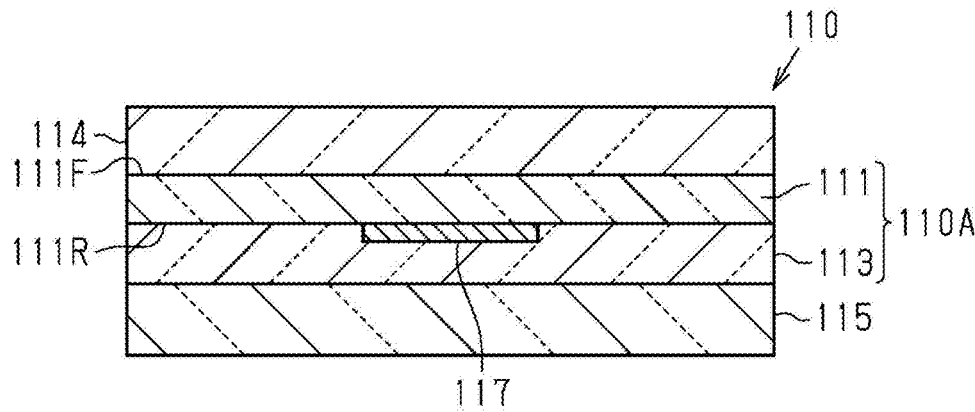
FIG. 10 is a cross-sectional view of a first example of a part of the examination marker including a verification part.
Figure 11:
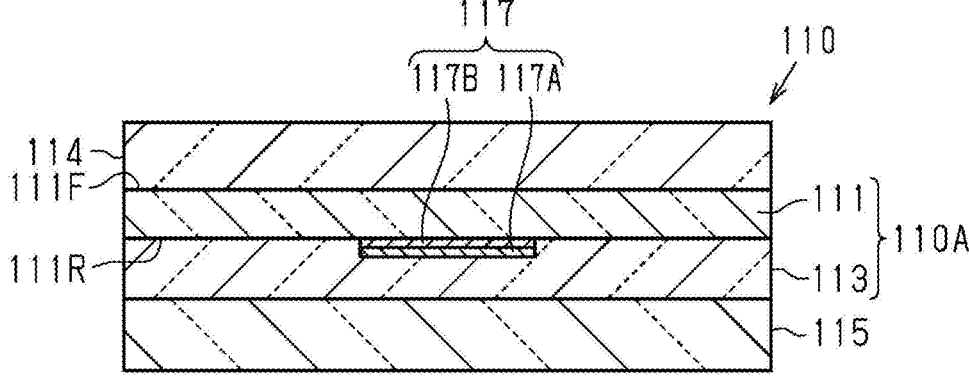
FIG. 11 is a cross-sectional view of a second example of a part of the examination marker including a verification part.

An embodiment of the examination marker will be described as a second embodiment of the present disclosure with reference to FIGS. 8 to 11. FIG. 8 shows a planar structure of the examination marker, as seen from a viewpoint facing the front surface of a base film included in the examination marker. FIG. 9 shows a cross-sectional structure of a part of the examination marker including a scanned part of the base film. In contrast to this, FIGS. 10 and 11 show a cross-sectional structure of a part of the examination marker including a peripheral part of the base film.

The examination marker is used for image diagnosis using microwaves. The examination marker of the present disclosure is used for mammography that is an example of image diagnosis using microwaves, for example. In the present disclosure, in particular, microwaves at a wavelength band of 1 GHz or more and 10 GHz or less are preferably used.

As shown in FIG. 8, an examination marker 110 includes a front surface 111F (see FIG. 9) and a non-conductive base film 111. In FIG. 8, a release film 114 is positioned on the frontmost surface of the examination marker 110 as described later. The base film 111 includes a scanned part 111A and a peripheral part 111B, as seen from a viewpoint facing the front surface 111F. The scanned part 111A is a part of the base film 111 to be scanned with a probe to obtain a signal for use in image diagnosis. The peripheral part 111B is a part of the base film 111 that surrounds the scanned part 111A.

The examination marker 110 includes a verification part 117 positioned at the peripheral part 111B. The microwave transmittance of the verification part 117 is lower than the microwave transmittance of the base film 111. The verification part 117 is an example of a first verification part. According to the examination marker 110, it is possible to determine the authenticity of the examination marker 110 by scanning the peripheral part 111B of the base film 111 with a probe emitting microwaves and checking if there is a portion of the peripheral part 111B where a received signal is attenuated.

The authenticity determination of the examination marker 110 can be performed before attaching the examination marker 110 to the examination subject. The authenticity determination is performed by an examiner in charge of mammography, for example. The examiner can check and determine whether the output waveform of a signal received by the probe is an output waveform obtained by scanning the verification part 117 of the examination marker 110 or an output waveform obtained by scanning a part other than the verification part 117 of the examination marker 110.

The examination marker 110 in the present embodiment includes a coordinate grid 112 and a marker 116. The coordinate grid 112 is positioned within the scanned part 111A as seen from a viewpoint facing the front surface 111F. That is, in the examination marker 110 including the coordinate grid 112, the part of the base film 111 inside the coordinate grid 112 is the scanned part 111A, and the part of the base film 111 outside the coordinate grid 112 is the peripheral part 111B, as seen from a viewpoint facing the front surface 111F. The base film 111 has a square shape as seen from a viewpoint facing the front surface 111F. The peripheral part 111B has an annular shape including the edge of the base film 111. In the example shown in FIG. 8, the scanned part 111A has a square shape, and the peripheral part 111B has a square ring shape. The verification part 117 is positioned at a corner of the base film 111.

The coordinate grid 112 includes a plurality of grid lines 112A. Each of the grid lines 112A extends along a scanning direction DS, and the plurality of grid lines 112A is aligned along an arrangement direction DA orthogonal to the scanning direction DS. In the present embodiment, the scanning direction DS is the horizontal direction in the plane of plane. The scanning direction DS is a direction in which the examination target is scanned by the examiner using a probe. As described above, the verification part 117 is positioned at a corner of the base film 111. Thus, in scanning the scanned part 111A using a probe to obtain a signal for generating an image, it is possible to suppress the verification part 117 from being scanned. Accordingly, it is possible to suppress occurrence of noise in the generated image due to scanning of the verification part 117.

In the present embodiment, the arrangement direction DA is the vertical direction in the plane of paper. In the arrangement direction DA, first grid lines 112A1 having a first color and second grid lines 112A2 having a second color are alternately aligned. The second color is different from the first color.

In performing scanning with a probe along the scanning direction DS, the examiner can alternately perform scanning along the first grid lines 112A1 and scanning along the second grid lines 112A2. Accordingly, it is possible to suppress the examiner from scanning the same grid line 112A a plurality of times or omitting to scan a certain grid line 112A. That is, according to the grid lines 112A, it is possible to reduce scanning errors that might be made by the examiner.

The first grid lines 112A1 may be red, for example, and the second grid lines 112A2 may be blue, for example. The first color that is the color of the first grid lines 112A1 and the second color that is the color of the second grid lines 112A2 are not limited to red and blue and can be arbitrarily set as far as they are different colors.

The coordinate grid 112 further includes a plurality of grid lines 112B that extends along the arrangement direction DA and are aligned along the scanning direction DS. The plurality of grid lines 112B forms a square grid together with the plurality of grid lines 112A described above, as seen from a viewpoint facing a plane over which the examination marker 110 spreads. In each grid line 112B, first segments 112B1 and second segments 112B2 are alternately aligned. In the arrangement direction DA, the first segments 112B1 and the second segments 112B2 are defined in each section sandwiched between one first grid line 112A1 and one second grid line 112A2 adjacent to each other. The first segments 112B1 have the first color as the first grid lines 112A1 do. The second segments 112B2 have the second color as the second grid lines 112A2 do.

The coordinate grid 112 further includes positional markers 112C. In the present embodiment, the positional markers 112C are numbers for use in specifying the position on the coordinate grid 112. The positional markers 112C include a plurality of numbers aligned along the scanning direction DS, for example. The plurality of numbers is positioned outside of the first grid line 112A1 that is positioned at the upper end in the arrangement direction DA. In the scanning direction DS, each of the numbers is positioned between two grid lines 112B or is positioned outside of the grid line 112B that is positioned at the end. The positional markers 112C include a plurality of numbers aligned along the arrangement direction DA, for example. The plurality of numbers is positioned outside of the grid line 112B positioned at the left end in the scanning direction DS. Each of the numbers is positioned between two grid lines 112A in the arrangement direction DA. The positional markers 112C are not limited to a plurality of numbers and may include a plurality of characters, for example.

Since the coordinate grid 112 includes the positional markers 112C, the accuracy of the examination can be further improved by the examiner referring to the positional markers 112C. If a lesion is found in the breast, the positional markers 112C can be used to specify the position of the lesion in the breast.

The coordinate grid 112 is printed using ink on the rear surface 111R (see FIG. 9) of the base film 111. The ink for printing the coordinate grid 112 can be any ink that is capable of printing the base film 111.

The marker 116 indicates a predetermined position on the coordinate grid 112. In the present embodiment, the predetermined position is the center of the coordinate grid 112. The marker 116 is a circular point that is positioned in the center of the coordinate grid 112. The shape of the marker 116 is not limited to a circle and can be arbitrarily set. The marker 116 may be formed by a plurality of portions separated from each other. As far as the marker 116 indicates the center of the coordinate grid 112, the marker 116 may be arranged at a position shifted from the center of the coordinate grid 112. The marker 116 may be printed using ink on the rear surface 111R of the base film 111 in the same manner as the coordinate grid 112.

According to the marker 116, at the time of use of the examination marker 110, coordinates indicated by the marker 116 can be superimposed on the breast at the specific position. According to the present embodiment, when the examiner attaches the examination marker 110 to the breast such that the marker 116 is positioned in the entire surrounding area of the nipple, the coordinate grid 112 can be positioned in the entire surrounding area of the nipple. Accordingly, the examiner can scan the entire breast in the circumferential direction of the nipple.

The width of the verification part 117 in the arrangement direction DA is preferably smaller than the distance between a pair of grid lines 112A1 in the arrangement direction DA, as seen from a viewpoint facing the front surface 111F. Accordingly, the verification part 117 can have a size that can be captured by scanning with a probe. The size of the verification part 117 may be equal to or smaller than one grid cell defined in the coordinate grid 112, as seen from a viewpoint facing the front surface 111F.

The verification part 117 can have any shape as seen from a viewpoint facing the front surface 111F of the base film 111. That is, the verification part 117 may have a square shape, a circular shape, or any other shape, for example. The verification part 117 may have a linear shape extending in a specific direction. The examination marker 110 may include a plurality of verification parts 117. In this case, the plurality of verification parts 117 may include the verification parts 117 of the same shape or may include the verification parts 117 of a first shape and the verification parts 117 of a second shape different from the first shape.

As shown in FIG. 9, the examination marker 110 includes the base film 111, an adhesive layer 113, the release film 114, and a protective film 115. The base film 111 includes the front surface 111F and the rear surface 111R opposite to the front surface 111F. The coordinate grid 112 described above is positioned on the rear surface 111R of the base film 111. The adhesive layer 113 is positioned on the rear surface 111R of the base film 111 to cover the coordinate grid 112. The release film 114 is laminated in a peelable manner on the front surface 111F of the base film 111. The protective film 115 is laminated in a peelable manner on the surface of the adhesive layer 113 opposite to the surface in contact with the base film 111. In the examination marker 110, the base film 111 and the adhesive layer 113 form a marker main body 110A.

The base film 111 preferably satisfies the following condition:

(Condition 2-1) The base film 111 has a tensile elongation at break of 130% or more and a 100% elongation tensile strength of 4 N/cm or less.

The marker main body 110A preferably satisfied the following condition:

(Condition 2-2) The moisture permeability prescribed in JIS Z 0208-1976 is 750 g/m2 day or more at a temperature of 40° C. and a relative humidity of 90%.

The base film 111 has a tensile elongation at break and a 100% elongation tensile strength suited for attachment to the examination target. Thus, according to the base film 111, it is easy to attach the examination marker 110 to the examination target.

The tensile elongation at break can be determined in conformity with JIS K 7161-1: 2014 (ISO 527-1) "Plastics—Determination of tensile properties—Part 1: General principles", and JIS K 7127: 1999 (ISO 527-3) "Plastics—Determination of tensile properties—Part 3: Test conditions for films and sheets".

If the target to be measured has no yield point, the tensile breaking strain is measured. If the target to be measured has a yield point, the nominal strain at tensile fracture is measured. These measurement values can be used to determine the tensile elongation at break.

The 100% elongation tensile strength is obtained by measuring the magnitude of a force applied to a test piece when the strain on the test piece has reached a prescribed value (100%) and dividing the magnitude of the force by the width of the test piece, as defined in JIS K 7161-1: 2014 (ISO 527-1) "Plastics—Determination of tensile properties—Part 1: General principles". The 100% elongation tensile strength (T) (N/cm) can be determined by the following equation:

$$T = F / W$$

where F is the measured magnitude (N) of the force, and W is the width (cm) of the test piece.

The moisture permeability is measured by a method in conformity with JIS Z 0208-1976 "Testing Methods for Determination of the Water Vapour Transmission Rate of Moisture-Proof Packaging Materials". Since the moisture permeability of the marker main body 110A satisfies the condition 2-2, when the marker main body 110A is attached to the examination target, it is possible to suppress the perspiration of the examination target.

The marker main body 110A can include a part of which the total light transmittance defined in JIS K 7361-1: 1997 "Plastics—Determination of the total luminous transmittance of transparent materials—Part 1: Single beam instrument" is 30% or more. Accordingly, it is possible to grasp the state of the surface of the breast via the part of the marker main body 110A with a total light transmittance of 30% or more. In the present embodiment, the part of the marker main body 110A other than the coordinate grid 112 is a transmission part with a total light transmittance of 30% or more. Therefore, it is possible to specify the positions of moles and spots on the breast by visual check or camera via the transmission part. Since moles and spots on the breast do not change in position, the positions of moles and spots on the breast are important in locating a lesion in the breast.

The base film 111 is made of a synthetic resin. The synthetic resin for forming the base film 111 may be a polyurethane resin, for example. This makes it possible to obtain the base film 111 that has excellent bonding adaptability and high moisture permeability. The thickness of the base film 111 may be 5 µm or more and 30 µm or less, for example. The base film 111 that is thin and made of a polyurethane resin can be stretched well even with small external force applied to the base film 111 for stretching the base film 111. Thus, the base film 111 can exhibit high conformability to the shape of the breast and high adhesion to the breast.

The base film 111 may be made of a synthetic resin other than a polyurethane resin. Examples of a synthetic resin other than a polyurethane resin include polyvinylidene fluoride resin, ethylene-vinyl acetate copolymer resin, polypropylene resin, polyethylene terephthalate resin, and the like.

The adhesive layer 113 is made of a synthetic resin as the base film 111 is. The synthetic resin for forming the adhesive layer 113 may be a polyurethane resin, for example. Forming the adhesive layer 113 from a polyurethane resin makes it possible to provide the adhesive layer 113 with high moisture permeability. The thickness of the adhesive layer 113 may be 5 μm or more and 25 μm or less, for example.

Each of the release film 114 and the protective film 115 is preferably a transparent or translucent film made of a synthetic resin. Each of the release film 114 and the protective film 115 is formed of a base film and a release layer, for example. The release layer is laminated on the base film. The release layer of the release film 114 is in contact with the front surface 111F of the base film 111. The release layer of the protective film 115 is in contact with the adhesive layer 113. The base film may be a polyethylene terephthalate film or the like, for example. The release layer may be a layer made of a silicone resin, for example. Each of the release film 114 and the protective film 115 may be formed of only a base film, and the surface of the base film in contact with another layer may be processed for enhancing peelability.

A part of the release film 114 may be subjected to half-cut processing. In other words, the release film 114 may have a slit that extends from the front surface of the release film 114 to the middle of the release film 114 in the thickness direction of the release film 114. The surface of the release film 114 opposite to the surface in contact with the base film 111 is the front surface.

The verification part 117 will be described in more detail with reference to FIGS. 10 and 11. FIG. 10 shows a first example of the verification part 117. On the other hand, FIG. 11 shows a second example of the verification part 117.

First Example

As shown in FIG. 10, the first example of the verification part 117 is positioned on the rear surface 111R of the base film 111 as the coordinate grid 112 is. The verification part 117 is sandwiched between the base film 111 and the adhesive layer 113. The verification part 117 is a print layer. The print layer is a cured body of transparent conductive ink. The conductive ink is an example of a conductive resin composition. In this case, the verification part 117 included in the genuine examination marker 110 is unlikely to be known. Thus, discriminating a genuine examination marker and a false examination marker by the presence or absence of the verification part increases the possibility that the discrimination result is correct. That is, since the verification part 117 included in the genuine examination marker 110 is unlikely to be known, even if the examination marker 110 is imitated, a false examination marker that is an imitation includes no verification part. Thus, it is possible to accurately discriminate between the genuine examination marker 110 and the false examination marker by performing authenticity determination using the verification part 117.

The transparent conductive ink contains a resin composition and a conductive filler. The resin composition may be a thermosetting resin, for example. The conductive ink contains, as the conductive filler, at least one of carbon nanotubes, silver nanowires, zinc oxide particles, and the like, for example. That is, the conductive ink may contain one or two or more of carbon nanotubes, silver nanowires, and zinc oxide particles. The conductive ink may contain conductive polymers as the conductive filler. The conductive polymers may be PEDOT/PSS, for example. This enables the conductive ink to be conductive and transparent. The total light transmittance of the verification part 117 is preferably 30% or more as with the base film 111 and the adhesive layer 113.

The thickness of the verification part 117 is 10 μm or more and 20 μm or less, for example. The thickness of the grid lines 112A1 and 112A2 included in the coordinate grid 112 is about 1 μm, for example. This makes it possible to suppress the sizes of concave and convex portions on the front surface 111F of the base film 111 to a degree that does not affect the accuracy of image diagnosis.

As described above, in the examination marker 110, the microwave transmittance of the verification part 117 is lower than the microwave transmittance of the base film 111. In the present embodiment, the microwave transmittance of the verification part 117 is lower than the microwave transmittance of the marker main body 110A. The microwave transmittances of the verification part 117, the base film 111, and the marker main body 110A can be measured by the method described below.

The microwave transmittance of the base film 111 can be calculated by the ratio of the microwave receiving strength with the base film 111 between a microwave oscillator and a microwave receiver to the microwave receiving strength without the base film 111 between the microwave oscillator and the microwave receiver. More specifically, the microwave receiving strength without the base film 111 is a first strength (S1), and the microwave receiving strength with the base film 111 is a second strength (S2). The percentage of the second strength to the first strength ((S2/S1)×100) is the microwave transmittance (%) of the base film 111.

The microwave transmittance of the marker main body 110A and the microwave transmittance of the verification part 117 can be measured in the same manner as the method for measuring the microwave transmittance of the base film 111. In the case of measuring the microwave transmittance of the verification part 117, the verification part 117 is formed on the base film 111, and then the microwave transmittance of the laminated body including the base film 111 and the verification part 117 is measured. Then, the microwave transmittance of the verification part 117 can be obtained from the microwave transmittance of the base film 111 and the microwave transmittance of the laminated body. The microwave transmittance of the verification part 117 can also be obtained from the material for forming the verification part 117.

The microwave transmittance of the verification part 117 to microwaves at a frequency of 2 GHz may be 0% or more and 30% or less, for example. The microwave transmittance of the base film 111 may be 70% or more. The microwave transmittance of the marker main body 110A may be 70% or more.

Second Example

As shown in FIG. 11, the second example of the verification part 117 is positioned on the rear surface 111R of the base film 111 as the first example of the verification part 117 is. The verification part 117 is sandwiched between the base film 111 and the adhesive layer 113. The verification part 117 includes a first print layer 117A and a second print layer 117B. The second print layer 117B covers the first print layer 117A as seen from a viewpoint facing the front surface 111F of the base film 111. The first print layer 117A is a cured body of conductive color ink.

The second print layer 117B may be a cured body of non-conductive ink having a color that can conceal the first print layer 117A. The non-conductive ink is an example of a non-conductive resin composition. As shown in FIG. 11, the second print layer 117B may be in contact with the rear surface 111R of the base film 111, and the first print layer 117A may be positioned on the second print layer 117B. The first print layer 117A may be in contact with the rear surface 111R of the base film 111, and the second print layer 117B may be positioned on the first print layer 117A.

According to the second example of the verification part 117, since the ink for forming the first print layer 117A is unlikely to be limited by ink color, it is possible to enhance the degree of freedom to select ink for forming the first print layer 117A. In addition, since the first print layer 117A is concealed by the second print layer 117B, the conductive verification part 117 included in the genuine examination marker 110 is unlikely to be known. Accordingly, discriminating the genuine examination marker 110 and the false examination marker by the presence or absence of the verification part increases the possibility that the discrimination result is correct. That is, as in the first example of the verification part 117, since the verification part 117 included in the genuine examination marker 110 is unlikely to be known, even if the examination marker 110 is imitated, a false examination marker that is an imitation includes no verification part. Thus, it is possible to accurately discriminate between the genuine examination marker 110 and the false examination marker by performing authenticity determination using the verification part 117.

The conductive color ink contains a resin composition and a conductive filler. The conductive ink contains, as the conductive filler, at least one of carbon, metal, and the like, for example. The carbon may be black lead or carbon black, for example. The metal may be any of nickel, copper, gold, silver, aluminum, zinc, nickel, tin, lead, chromium, platinum, palladium, tungsten, and molybdenum, or an alloy or mixture including two or more of them. Alternatively, the conductive filler may be a conductive compound among the above-described metallic compounds. Accordingly, the conductive ink can be conductive and have a predetermined color.

The non-conductive color ink can conceal the conductive color ink. The non-conductive ink can have the same hue as that of the conductive ink and may represent a less bright color than that of the conductive ink, for example. The non-conductive ink may represent the color of the same hue, brightness, and saturation as those of the conductive ink. The non-conductive ink contains a resin composition and a coloring composition. The resin composition may be a thermosetting resin, for example. The coloring composition may be a colorant, pigment, or the like, for example.

The thickness of the verification part 117 is the sum of the thickness of the first print layer 117A and the thickness of the second print layer 117B. The thickness of the first print layer 117A may be equal to the thickness of the first example of the verification part 117. The thickness of the second print layer 117B may be equal to the thickness of the grid lines 112A1 and 112A2 included in the coordinate grid 112, for example. This makes it possible to suppress the sizes of concave and convex portions on the surface 111F of the base film 111 to a degree that does not affect the accuracy of image diagnosis.

The size of the second print layer 117B may be equal to the size of the first print layer 117A, and the second print layer 117B may cover the entire first print layer 117A, as seen from a viewpoint facing the front surface 111F of the base film 111. Alternatively, the second print layer 117B may be larger than the first print layer 117A, and the first print layer 117A may be positioned within the second print layer 117B, as seen from a viewpoint facing the front surface 111F of the base film 111.

In the second example of the verification part 117, the microwave transmittance of the first print layer 117A is lower than the microwave transmittance of the base film 111 so that the microwave transmittance of the verification part 117 is lower than the microwave transmittance of the base film 111. In the present embodiment, the microwave transmittance of the verification part 117 is lower than the microwave transmittance of the marker main body 110A. The microwave transmittance of the first print layer 117A may be 0% or more and 30% or less to microwaves at a frequency of 2 GHz, for example.

As described above, according to the second embodiment of the examination marker, the following advantageous effects can be obtained.

(2-1) According to the examination marker 110, it is possible to determine the authenticity of the examination marker 110 by scanning the peripheral part 111B of the base film 111 with a probe emitting microwaves and checking if there is a portion of the peripheral part 111B where the received signal is attenuated.

(2-2) The verification part 117 is positioned at a corner of the base film 111. Thus, in scanning the scanned part 111A using a probe to obtain a signal for generating an image, it is possible to suppress the verification part 117 from being scanned. Accordingly, it is possible to suppress occurrence of noise in the generated image due to scanning of the verification part 117.

(2-3) According to the first example of the verification part 117, the verification part 117 included in the genuine examination marker 110 is unlikely to be known. Thus, discriminating the genuine examination marker 110 and the false examination marker by the presence or absence of the verification part 117 increases the possibility that the discrimination result is correct.

(2-4) According to the second example of the verification part 117, the ink for forming the first print layer 117A is unlikely to be limited by ink color, and it is possible to enhance the degree of freedom to select ink for forming the first print layer 117A.

Modifications of Second Embodiment

The second embodiment described above can be carried out in modified manners as described below.

[Coordinate Grid]

Figure 12:
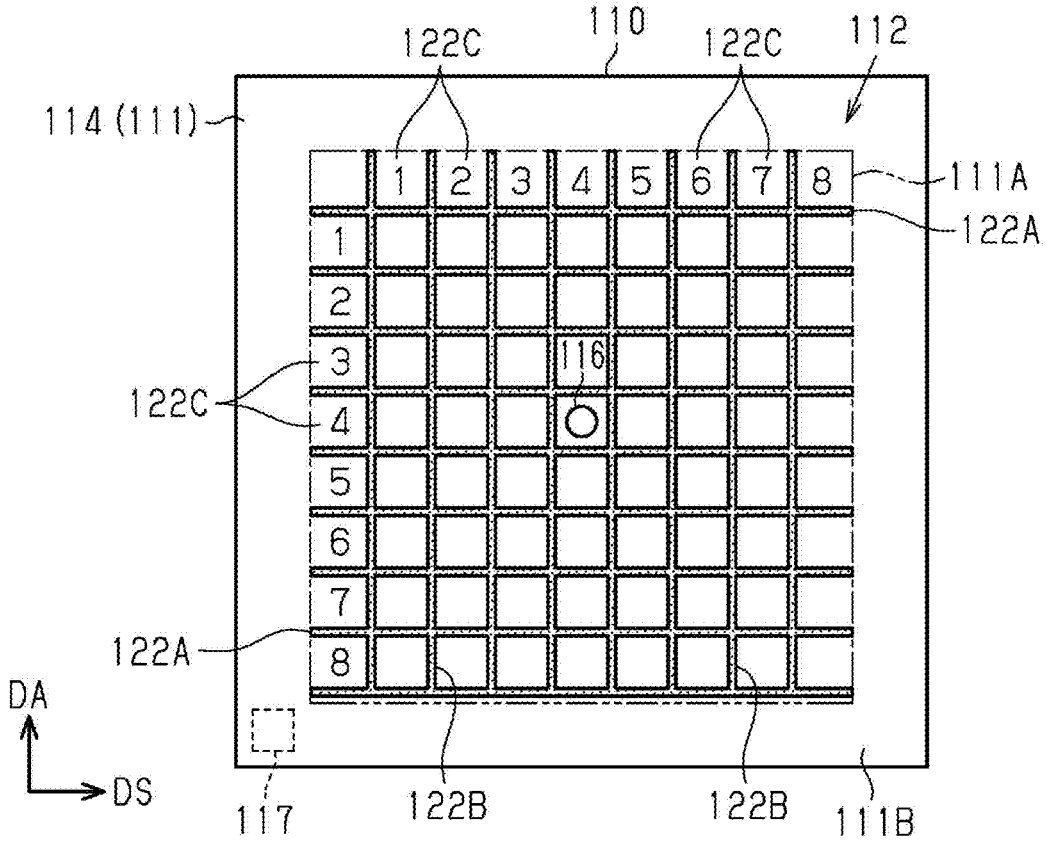
FIG. 12 is a plan view of a structure of a modification of an examination marker.

As shown in FIG. 12, the plurality of grid lines 122A and the plurality of grid lines 122B may have the same color. In this case, since the plurality of grid lines 122A and 122B can be made of the same material, it is easy to manufacture the examination marker 110. The coordinate grid 112 includes positional markers 122C and a marker 116. The positional markers 122C and the marker 116 have the same color as the grid lines 122A and 122B.

In the plurality of grid lines 122A, adjacent grid lines 122A may be made different in external appearance. Accordingly, it is possible to suppress scanning errors that might be made by the examiner, as in the case where the colors of adjacent grid lines 122A in the coordinate grid 112 are made different.

In the case of making different the outer appearances of adjacent grid lines 122A, solid grid lines 122A and broken grid lines 122A may be alternately arranged, for example. In this case, in the plurality of grid lines 122B, solid grid lines 122B and broken grid lines 122B may be alternately arranged as well.

In the coordinate grid 112, the plurality of grid lines 122A may be arranged at intervals of the same width as the width of the grid lines 122A in the arrangement direction DA. In this case, the grid lines 122A preferably have the width of the same degree as the distance between two grid lines 112A shown in FIG. 8, for example. In this case, the grid lines 122A may be formed by solid printing or may be formed by a plurality of dots. Accordingly, since the grid lines 122A and the transparent parts are alternately positioned in the coordinate grid 112, it is possible to suppress scanning errors that might be made by the examiner as in the case with the coordinate grid 112.

[Verification Part]

The second example of the verification part 117 may include two second print layers 117B.

In this case, the two second print layers 117B sandwich the first print layer 117A in the thickness direction of the first print layer 117A. The second print layers 117B can conceal the first print layer 117A.

If the first print layer 117A is sandwiched between the two second print layers 117B, the non-conductive ink for forming the second print layers 117B may have the same hue as that of the conductive ink and may represent a less bright color than that of the conductive ink, for example.

The non-conductive ink may represent a color of the same hue, brightness, and chroma as those of the conductive ink. The non-conductive ink may have a black color. When the non-conductive ink has these colors, the non-conductive ink can conceal the conductive ink. The non-conductive ink may conceal the conductive ink by having a thickness to a degree that the conductive ink covered with the non-conductive ink is not seen through.

In this case, the following advantageous effect can be obtained.

(2-5) Since the first print layer 117A is sandwiched between the pair of second print layers 117B, the presence of the first print layer 117A between the pair of second print layers 117B is concealed by the second print layers 117B even when the examination marker 110 is observed from either the front or back side. Thus, the first print layer 117A included in the examination marker 110 is unlikely to be known.

The verification part 117 may be an alignment mark for positioning the coordinate grid 112 with respect to the base film 111.

The verification part 117 may be positioned on the front surface 111F of the base film 111. Even in this case, since the verification part 117 is positioned at the peripheral part 111B of the base film 111, it is possible to suppress occurrence of noise in the image due to the verification part 117.

The verification part 117 may not be positioned on the base film 111 but may be positioned on any of the adhesive layer 113, the release film 114, and the protective film 115. If the verification part 117 is positioned on the adhesive layer 113, the verification part 117 is positioned within the peripheral part 111B, as seen from a viewpoint facing the front surface 111F of the base film 111. If the verification part 117 is positioned on the release film 114 or the protective film 115, the verification part 117 may be positioned at any part on the film 114 or 115.

The verification part 117 is preferably positioned on the surface of the film 114 or 115 opposite to the surface in contact with the marker main body 110A. If the verification part 117 is positioned on any of the films 114 and 115, when the film 114 or 115 is peeled off from the marker main body 110A, the verification part 117 is separated from the marker main body 110A.

[Examination Marker]

The examination marker 110 may have any shape other than a square shape as seen from a viewpoint facing the front surface 111F of the base film 111. Even in this case, the verification part 117 is positioned at the peripheral part 111B that is located outside of the scanned part 111A and surrounds the scanned part 111A.

The examination marker in the second embodiment can be carried out in combination with the examination marker in the first embodiment.

Third Embodiment

An embodiment of an examination marker set will be described with reference to FIGS. 13 to 15 as a third embodiment of the present disclosure. The examination marker set described below includes the examination marker 110 in the second embodiment and an auxiliary marker.

Thus, hereinafter, the auxiliary marker will be described in detail while description of the examination marker 110 will be omitted.

Figure 13:
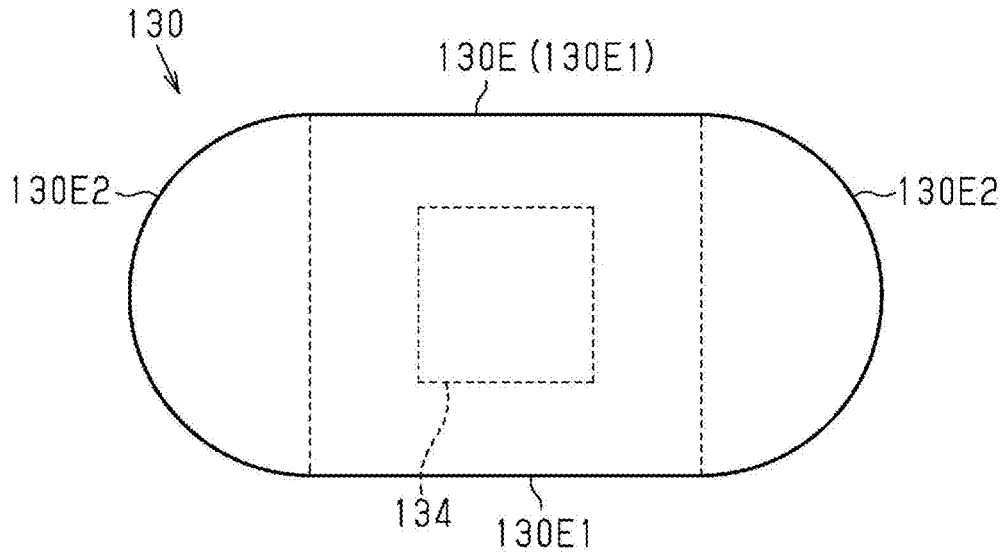
FIG. 13 is a plan view of a structure of an auxiliary marker included in an examination marker in a third embodiment.

FIG. 13 shows a planar structure of the auxiliary marker. An auxiliary marker 130 shown in FIG. 13 is used together with the examination marker 110 to be attached to the examination target for image diagnosis using microwaves. The auxiliary marker 130 constitutes an examination marker set together with the examination marker 110. At the time of use of the auxiliary marker 130, that is, at the time of image diagnosis, the auxiliary marker 130 is positioned between the examination marker 110 and the examination target and is pressed by the examination marker 110 toward the examination target. In the present embodiment, the examination target is a breast, and the examination marker 110 and the auxiliary marker 130 are markers for used in mammography using microwaves.

The auxiliary marker 130 includes a non-conductive marker main body 130A (see FIG. 14), a protective film 133 (see FIG. 14), and a verification part 134. The protective film 133 is laminated on the marker main body 130A so as to be peelable from the marker main body 130A.

The verification part 134 is positioned on the protective film 133. The microwave transmittance of the verification part 134 is lower than the microwave transmittance of the laminated body of the marker main body 130A and the protective film 133. The verification part 134 is an example of a second verification part. According to the examination marker set, as in the case of the examination marker 110, it is possible to determine the authenticity of the auxiliary marker 130 and the authenticity of a combination of the examination marker 110 and the auxiliary marker 130 by scanning the auxiliary marker 130 with a probe.

The verification part 134 may be positioned at any position on the protective film 133 as seen from a viewpoint facing a plane over which the auxiliary marker 130 extends. The verification part 134 may have any shape as seen from a viewpoint facing the plane over which the auxiliary marker 130 extends. The verification part 134 may have a square shape, may have a circular shape, or may have any other shape, for example.

The auxiliary marker 130 may have an oval shape or a capsular shape as seen from a viewpoint facing the plane over which the auxiliary marker 130 extends. In the present embodiment, the auxiliary marker 130 has a capsular shape. In the present embodiment, since the protective film 133 has the same shape as the marker main body 130A as seen from a viewpoint facing the plane over which the auxiliary marker 130 spreads, the auxiliary marker 130 has a capsule shape. The protective film 133 may have a shape different from that of the marker main body 130A. However, in order to keep clean the entire marker main body 130A, the protective film 133 preferably has a size larger than that of the marker main body 130A.

The capsular shape refers to a shape in which a rectangle and two semi-circles are combined or a shape in which a rectangle and two semi-ellipses are combined. More specifically, the capsular shape refers to a shape in which semi-circles or semi-ellipses are connected to short sides of a rectangle.

In the present embodiment, the auxiliary marker 130 has a shape in which a rectangle and two semi-circles are combined. Thus, the auxiliary marker 130 has an edge 130E formed by two straight parts 130E1 and two arcuate parts 130E2. In the edge of the auxiliary marker 130, the two straight parts 130E1 are arranged to be parallel to each other. First end portions of the straight parts 130E1 are connected by one arcuate part 130E2, and second end portions of the straight parts 130E1 are connected by the other arcuate part 130E2.

The verification part 134 will be described in more detail with reference to FIGS. 14 and 15. FIG. 14 shows a first example of the verification part 134. FIG. 15 shows a second example of the verification part 134. Hereinafter, after description of the verification part 134, the parts of the auxiliary marker 130 other than the verification part 134 will be described.

First Example

Figure 14:
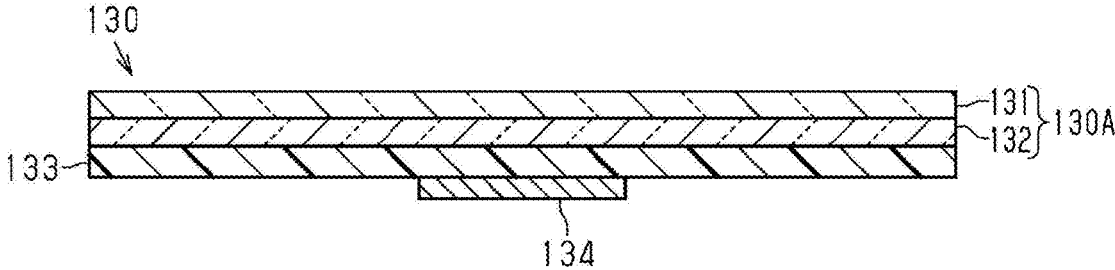
FIG. 14 is a cross-sectional view of a first example of a structure of an auxiliary marker.

As shown in FIG. 14, the auxiliary marker 130 includes a base film 131, an adhesive layer 132, and the protective film 133. The adhesive layer 132 is laminated on the base film 131 and attached to the breast. The laminated body of the base film 131 and the adhesive layer 132 is the marker main body 130A. The protective film 133 is laminated on the adhesive layer 132. The protective film 133 covers the entire adhesive layer 132. The verification part 134 is positioned on the surface of the protective film 133 opposite to the surface in contact with the adhesive layer 132. Thus, at the time of use of the auxiliary marker 130, when the protective film 133 is peeled off from the adhesive layer 132, the verification part 134 is removed from the marker main body 130A together with the protective film 133.

The first example of the verification part 134 is a print layer as with the first example of the verification part 117 of the auxiliary marker 110. The print layer is a cured body of transparent conductive ink. In this case, the verification part 134 included in the genuine auxiliary marker 130 is unlikely to be known. Thus, discriminating the genuine auxiliary marker 130 and the false auxiliary marker by the presence or absence of the verification part 134 increases the possibility that the discrimination result is correct. That is, since the verification part 134 included in the genuine auxiliary marker 130 is unlikely to be known, even if the auxiliary marker 130 is imitated, a false auxiliary marker that is an imitation includes no verification part. Thus, it is possible to accurately discriminate between the genuine auxiliary marker 130 and the false auxiliary marker by performing authenticity determination using the verification part 134.

The transparent conductive ink contains a resin composition and a conductive filler. The resin composition may be a thermosetting resin, for example. The conductive ink contains, as the conductive filler, at least one of carbon nanotubes, silver nanowires, zinc oxide particles, and the like, for example. That is, the conductive ink may contain one or two or more of carbon nanotubes, silver nanowires, and zinc oxide particles. The conductive ink may contain a conductive polymer as the conductive filler. The conductive polymer may be PEDOT/PSS, for example. This enables the conductive ink to be conductive and transparent. The total light transmittance of the verification part 134 is preferably equal to the total light transmittance of the marker main body 130A and the total light transmittance of the protective film 133. The total light transmittance of the verification part 134 is preferably 30% or more.

The microwave transmittance of the laminated body of the marker main body 130A and the protective film 133 can be measured by a method similar to the method for measuring the microwave transmittance of the base film 111 included in the examination marker 110. The microwave transmittance of the laminated body of the marker main body 130A and the protective film 133 may be 70% or more with respect to microwaves at a frequency of 2 GHz, for example.

The microwave transmittance of the verification part 134 may be 0% or more or 30% or less as with the verification part 117 described above.

Second Example

Figure 15:
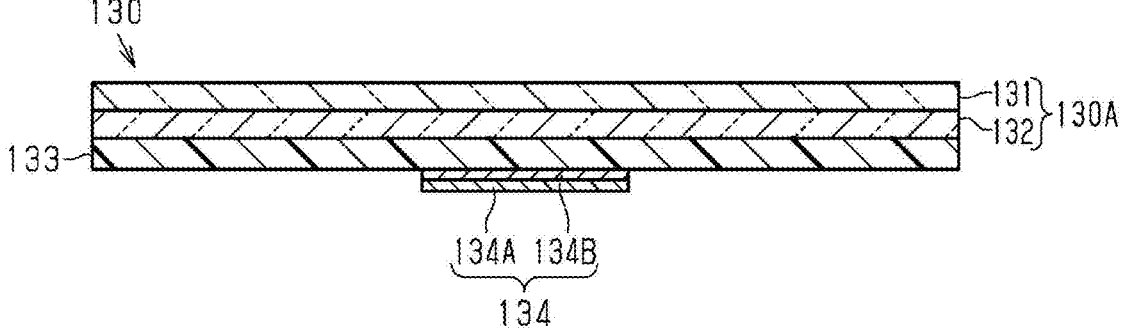
FIG. 15 is a cross-sectional view of a second example of a structure of the auxiliary marker.

As shown in FIG. 15, like the first example of the verification part 134, the second example of the verification part 134 is positioned on the surface of the protective film 133 opposite to the surface in contact with the adhesive layer 132. As with the second example of the verification part 117 of the examination marker 110, the second example of the verification part 134 includes a first print layer 134A and a second print layer 134B. The second print layer 134B covers the first print layer 134A as seen from a viewpoint facing a plane over which the base film 131 spreads. The first print layer 134A is a cured body of conductive color ink. The second print layer 134B is a cured body of non-conductive ink having a color that can conceal the first print layer 134A. As shown in FIG. 15, the second print layer 134B may be in contact with the base film 131, and the first print layer 134A may be positioned on the second print layer 134B. The first print layer 134A may be in contact with the base film 131, and the second print layer 134B may be positioned on the first print layer 134A.

According to the second example of the verification part 134, the ink for forming the first print layer 134A is unlikely to be limited by ink color, and it is possible to enhance the degree of freedom to select ink for forming the first print layer 134A. In addition, since the first print layer 134A is concealed by the second print layer 134B, the conductive verification part 134 included in the genuine auxiliary marker 130 is unlikely to be known. Accordingly, discriminating the genuine auxiliary marker 130 and the false auxiliary marker by the presence or absence of the verification part 134 increases the possibility that the discrimination result is correct. That is, as in the first example of the verification part 134, since the verification part 134 included in the genuine auxiliary marker 130 is unlikely to be known, even if the auxiliary marker 130 is imitated, a false examination marker that is an imitation includes no verification part. Thus, it is possible to accurately discriminate between the genuine auxiliary marker 130 and the false auxiliary marker by performing authenticity determination using the verification part 134.

The conductive color ink contains a resin composition and a conductive filler. The conductive ink contains, as the conductive filler, at least one of carbon, metal, and the like, for example. That is, the conductive ink may contain, as the conductive filler, only one of carbon and a metal or two or more of them, for example. The carbon may be black lead or carbon black, for example. The metal may be any of nickel, copper, gold, silver, aluminum, zinc, nickel, tin, lead, chromium, platinum, palladium, tungsten, and molybdenum, or an alloy or mixture including two or more of these. Alternatively, the conductive filler may be a conductive compound among the above-described metallic compounds. Accordingly, the conductive ink can be conductive and have a predetermined color. The non-conductive color ink can conceal the conductive color ink. The non-conductive ink may have the same hue as that of the conductive ink and may represent a less bright color than that of the conductive ink, for example. The non-conductive ink may represent a color of the same hue, brightness, and chroma as those of the conductive ink. The non-conductive ink contains a resin composition and a coloring composition. The resin composition may be a thermosetting resin, for example. The coloring composition may be a colorant, pigment, or the like, for example.

The size of the second print layer 134B may be equal to the size of the first print layer 134A, and the second print layer 134B may cover the entire first print layer 134A, as seen from a viewpoint facing a plane over which the base film 131 spreads. Alternatively, the second print layer 134B may be larger than the first print layer 134A, and the first print layer 134A may be positioned within the second print layer 134B, as seen from a viewpoint facing a plane over which the base film 131 spreads.

In the second example of the verification part 134, the microwave transmittance of the first print layer 134A is lower than the microwave transmittance of the laminated body of the marker main body 130A and the protective film 133. Accordingly, the microwave transmittance of the verification part 134 is lower than the microwave transmittance of the laminated body of the marker main body 130A and the protective film 133. The microwave transmittance of the first print layer 134A may be 0% or more and 30% or less to microwaves at a frequency of 2 GHz, for example.

The marker main body 130A shown in FIGS. 14 and 15 preferably satisfies the following condition 3-1 and condition 3-2:

(Condition 3-1) The base film 131 has a thickness of 20 μm or less.

(Condition 3-2) The base film 131 has a tensile modulus of 1 GPa or more.

When the marker main body 130A is attached to the breast so as to cover a nipple of the breast, the marker main body 130A can adhere to the breast while pressing the nipple in a direction in which to bring the nipple down in profile due to the tensile modulus of the base film 131. According to the auxiliary marker 130, applying the auxiliary marker 130 to the breast moderates the difference in height of the breast, so that it is possible to enhance the smoothness of scanning with a probe.

The tensile modulus is calculated in conformity with JIS K 7127: 1999 (ISO 527-3: 1995) "Plastics—Determination of tensile properties—Part 3: Test conditions for films and sheets" and JIS K 7161-1: 2014 (ISO 527-1: 2012) "Plastics-Determination of tensile properties-Part 1: General principles". The tensile modulus is defined in JIS K 7161-1: 2014, 3.9. The tensile modulus is calculated by the following equation (1) described in the above standard, 10 "Expression of Calculation and Test Results", 10.3.2 "Gradient from Two Points". The strain ε in the equation (1) is defined in the standard 3.7, and is calculated by the following equation (2) described in 10.2.1 "Strain Determined by Extensometer":

$$Et = (\sigma2 - \sigma1)/(\varepsilon2 - \varepsilon1) \qquad \text{Equation (1)}$$

$$\varepsilon = \Delta L0/L0 \qquad \text{Equation (2)}$$

In the equation (1), Et is elastic modulus (MPa), σ1 is a stress (MPa) with distortion ε1=0.0005 (0.05%), and σ2 is a stress (MPa) with distortion ε2=0.0025 (0.25%). In the equation (2), ε is distortion (%), L0 is a gauge length (mm) of a test piece, and ΔL0 is an increase amount (mm) of the gauge length of the test piece.

The auxiliary marker 130 further preferably satisfies the following condition 3-3 and condition 3-4:

(Condition 3-3) The adhesive layer 132 has a thickness of 25 μm or less.

(Condition 3-4) The marker main body 130A has a peel strength of 1.5 N/25 mm or more when the adhesive layer 132 is attached to a stainless steel test plate.

The peel strength has a value prescribed in JIS Z 0237: 2009. The peel strength is measured by a method in conformity with JIS Z 0237: 2009 "Testing Methods of Pressure-Sensitive Adhesive Tapes and Sheets". The peel strength is measured as in the standard 10.4.1 "Method 1: 180° Peel Adhesion to Test Plate". When the marker main body 130A satisfies the condition 3-3 and the condition 3-4, the adhesion of the adhesive layer 132 suppresses gaps between the breast and the adhesive layer 132. This further enhances the smoothness of scanning with a probe.

The marker main body 130A preferably includes a portion that has a total light transmittance of 30% or more and enables visual examination of the breast via the marker main body 130A. In the present embodiment, the entire marker main body 130A has a total light transmittance of 30% or more. Alternatively, only a portion of the marker main body 130A has a total light transmittance of 30% or more and enables visual examination of the breast via the marker main body 130A. Accordingly, it is possible to at least partially understand the state of the portion of the breast to which the marker main body 130A is attached via the marker main body 130A. If the entire marker main body 130A has a total light transmittance of 30% or more as in the present embodiment, it is possible to grasp the state of the entire part of the breast to which the marker main body 130A is attached via the marker main body 130A.

The base film 131 is formed of any of various synthetic resins. The synthetic resin may be a polyurethane resin (PU), an ethylene-vinyl acetate copolymer resin (EVA), a polyethylene resin (PE), a polypropylene resin (PP), a polyethylene terephthalate resin (PET), or the like, for example. Among these synthetic resins, PET is preferably used to form the base film 131. This makes it possible to enhance the tensile modulus of the base film 131 while keeping the thickness of the base film 131 at 20 μm or less. The base film 131 may be transparent or translucent. The total light transmittance of the base film 131 should be at least 30% throughout the base film 131.

The adhesive layer 132 is formed of any of various adhesives. The adhesive layer 132 may be formed of a urethane-based adhesive, for example. When the adhesive layer 132 is formed of a urethane-based adhesive, it is possible to set the peel strength of the marker main body 130A to 1.5 N/25 mm or more while keeping the thickness of the adhesive layer 132 at 25 μm or less. The adhesive layer 132 may be transparent or translucent. The total light transmittance of the entire adhesive layer 132 is preferably 30% or more.

The protective film 133 is formed of any of various resins. The synthetic resin may be PU, EVA, PE, PP, PET, or the like, for example. The protective film 133 is preferably higher in rigidity than the base film 131. The protective film 133 may be transparent or translucent. The total light transmittance of the protective film 133 is preferably 30% or more.

As described above, according to an embodiment of the examination marker set, it is possible to obtain, in addition to the advantageous effects (2-1) to (2-4) described above, the following advantageous effect:

(3-1) According to the examination marker set, as with the examination marker 110, it is possible to determine the authenticity of the auxiliary marker 130 and the authenticity of a combination of the examination marker 110 and the auxiliary marker 130 by scanning the auxiliary marker 130 with a probe.

Modification Examples of Third Embodiment

The foregoing embodiment can be carried out in modified manners as described below.
[Verification Part]

The second example of the verification part 134 may include two second print layers 134B. In this case, the two second print layers 134B sandwich the first print layer 134A in the thickness direction of the first print layer 134A. If the first print layer 134A is sandwiched between the two second print layers 134B, the non-conductive ink for forming the second print layers 134B may have the same hue as that of the conductive ink and may represent a less bright color than that of the conductive ink, for example. The non-conductive ink may represent a color of the same hue, brightness, and chroma as those of the conductive ink. The non-conductive ink may have a black color. When the non-conductive ink has these colors, the non-conductive ink can conceal the conductive ink. The non-conductive ink may conceal the conductive ink by having a thickness to a degree that the conductive ink covered with the non-conductive ink is not seen through.

The verification part 134 may be positioned on the surface of the protective film 133 in contact with the adhesive layer 132, as far as when the protective film 133 is peeled off from the marker main body 130A, the verification part 134 can be removed together with the protective film 133 from the marker main body 130A.
[Examination Marker]

The examination marker included in the examination marker set in the third embodiment can be carried out in combination with the examination marker in the first embodiment.

According to the embodiments and modification examples described above, it is possible to derive technical ideas described in Supplementary Notes as follows:
[Supplementary Note 1]

An examination marker for use in image diagnosis using microwaves, the examination marker including: a non-conductive base film that has a front surface and includes a scanned part that is to be scanned with a probe to obtain a signal for use in image diagnosis and a peripheral part that surrounds the scanned part, as seen from a viewpoint facing the front surface; and a verification part that is positioned at the peripheral part and contains a conductive resin composition, wherein the microwave transmittance of the verification part is lower than the microwave transmittance of the base film.

According to the examination marker, when the peripheral part of the base film is scanned with a probe emitting microwaves, it is possible to determine the authenticity of the examination marker by determining whether there is a portion of the peripheral part where the received signal is attenuated.
[Supplementary Note 2]

An examination marker for use in image diagnosis using microwaves, the examination marker including: a marker main body to be attached to a target of the image diagnosis; a film that is laminated on the marker main body so as to be capable of peeling off from the marker main body; and a verification part that is positioned on the film, wherein the microwave transmittance of the verification part is lower than the microwave transmittance of a laminated body of the marker main body and the film, and when the film is peeled off from the marker main body, the verification part is separated from the marker main body.

According to the examination marker, the examination marker includes the verification part. Therefore, it is possible to determine the authenticity of the examination marker by scanning the examination marker with a probe emitting microwaves and checking if there is a portion of the examination marker where the received signal is attenuated.

REFERENCE SIGNS LIST

10 . . . Examination marker; 10A, 10B . . . Marker main body; 11 . . . Base film; 12 . . . Coordinate grid; 12A . . . Grid line; 12A1 . . . First grid line; 12A2 . . . Second grid line.

What is claimed is:

1. An examination marker for use in diagnostic imaging using microwaves, wherein
    the examination marker comprises a marker main body to be attached to a human breast,
    the marker main body configured to display an index on the marker main body for use in scanning the human breast and to deform following a shape of the human breast,
    the marker consists of (a) a non-conductive base film that has a front surface and includes a scanned part that is to be scanned with a probe to obtain a signal for use in image diagnosis and a peripheral part that surrounds the scanned part, as seen from a viewpoint facing the front surface; (b) a verification part that is positioned at the peripheral part and consists of a conductive resin composition, (c) a coordinate grid,
    the base film has a relative permittivity of 10 or less to microwaves at a frequency of 1 GHz,
    the base film has a thickness of 5 to 300 μm; and
    a microwave transmittance of the verification part is lower than a microwave transmittance of the base film.

2. The examination marker of claim 1, wherein
    the base film has a tensile elongation at break of 130% or more and a 100% elongation tensile strength of 4N/cm or less.

3. The examination marker of claim 1, wherein
    the marker main body has a moisture permeability according to JIS Z 0208-1976 of 750 g/m$^2$ day or more at a temperature of 40° C. and a relative humidity of 90%.

4. The examination marker of claim 1, wherein the coordinate grid includes a plurality of grid lines that extends along a first direction in which the examination target is to be scanned and a plurality of grid lines that is aligned along a second direction orthogonal to the first direction, and the plurality of grid lines includes a first grid line having a first color and a second grid line having a second color different from the first color, and the first grid line and the second grid line are alternately aligned along the second direction.

5. The examination marker of claim 1, the coordinate grid includes a plurality of grid lines that extends along a first direction in which the examination target is to be scanned and is aligned along a second direction orthogonal to the first direction, and the plurality of grid lines has the same color.

6. The examination marker of claim 1, further comprising a marker indicating predetermined coordinates in the coordinate grid.

7. The examination marker of claim 1, wherein the verification part is a print layer, and the print layer is made of a cured body of the conductive resin composition that is transparent.

8. The examination marker of claim 1, wherein the verification part includes a first print layer and a second print layer that covers the first print layer as seen from a viewpoint facing the front surface, the first print layer is a cured body of the colored conductive resin composition, and the second print layer is a cured body of a non-conductive resin composition that has a color capable of concealing the first print layer.

9. The examination marker of claim 1, wherein the verification part includes a first print layer and a pair of second print layers, in a thickness direction of the first print layer, the pair of second print layers sandwiches the first print layer, the first print layer is a cured body of the colored conductive resin composition, the second print layers are cured bodies of a non-conductive resin composition, and the second print layers are capable of concealing the first print layer.

10. The examination marker of claim 1, wherein as seen from a viewpoint facing the front surface, the base film has a square shape, the peripheral part has an annular shape including an edge of the base film, and the verification part is positioned at a corner of the base film.

11. An examination marker set, comprising:

the examination marker of claim 1; and an auxiliary marker that is positioned between the examination marker and an examination target during diagnostic imaging using microwaves and is pressed by the examination marker toward the examination target, wherein the verification part includes a first verification part, the auxiliary marker includes:

a non-conductive marker main body;

a protective film that is laminated on the marker main body so as to be peelable from the marker main body; and a second verification part that is positioned on the protective film and includes a conductive resin composition, wherein a microwave transmittance of the second verification part is lower than a microwave transmittance of a laminated body of the marker main body and the protective film.

12. The examination marker of claim 1, wherein the base film has a tensile elongation at break of 130% or more and a 100% elongation tensile strength of 4N/cm or less and the marker main body has a moisture permeability according to JIS Z 0208-1976 of 750 $g/m^2$ day or more at a temperature of 40° C. and a relative humidity of 90%.

13. The examination marker of claim 1, wherein the base film has a tensile elongation at break of 130% or more and a 100% elongation tensile strength of 4N/cm or less and wherein as seen from a viewpoint facing the front surface, the base film has a square shape, the peripheral part has an annular shape including an edge of the base film, and the verification part is positioned at a corner of the base film.

14. The examination marker of claim 1, wherein the marker main body has a moisture permeability according to JIS Z 0208-1976 of 750 $g/m^2$ day or more at a temperature of 40° C. and a relative humidity of 90% and wherein as seen from a viewpoint facing the front surface, the base film has a square shape, the peripheral part has an annular shape including an edge of the base film, and the verification part is positioned at a corner of the base film.

15. The examination marker of claim 1, wherein the base film has a tensile elongation at break of 130% or more and a 100% elongation tensile strength of 4N/cm or less, the marker main body has a moisture permeability according to JIS Z 0208-1976 of 750 $g/m^2$ day or more at a temperature of 40° C. and a relative humidity of 90% and wherein as seen from a viewpoint facing the front surface, the base film has a square shape, the peripheral part has an annular shape including an edge of the base film, and the verification part is positioned at a corner of the base film.

16. An examination marker for use in diagnostic imaging using microwaves, wherein the examination marker comprises a marker main body to be attached to a human breast, the marker main body configured to display an index on the marker main body for use in scanning the human breast and to deform following a shape of the human breast, the marker consists of (a) a non-conductive base film that has a front surface and includes a scanned part that is to be scanned with a probe to obtain a signal for use in image diagnosis and a peripheral part that surrounds the scanned part, as seen from a viewpoint facing the front surface; (b) a verification part that is positioned at the peripheral part and consists of a conductive resin composition, (c) a coordinate grid and (d) an adhesive layer, the base film has a relative permittivity of 10 or less to microwaves at a frequency of 1 GHz, the base film has a thickness of 5 to 300 μm; and a microwave transmittance of the verification part is lower than a microwave transmittance of the base film.

* * * * *